United States Patent [19]
Moghaddam et al.

[11] Patent Number: 5,972,718
[45] Date of Patent: Oct. 26, 1999

[54] METHOD OF DETECTING HEPARIN-INDUCED THROMBOCYTOPENIA

[75] Inventors: Manouchehr Moghaddam, Waukesha; Gian Visentin, Shorewood; Richard H. Aster, Milwaukee; Benjamin W. Boldt, Elm Grove, all of Wis.

[73] Assignees: The Blood Center Research Foundation, Milwaukee; Genetics Testing Institute, Brookfield, both of Wis.

[21] Appl. No.: 08/803,734

[22] Filed: Feb. 21, 1997

Related U.S. Application Data

[60] Provisional application No. 60/012,445, Feb. 28, 1996.

[51] Int. Cl.$^6$ .................................................. G01N 33/53
[52] U.S. Cl. .......................... 436/506; 436/518; 436/501; 436/808; 436/69; 435/13; 435/810; 435/975; 521/29; 530/388.23
[58] Field of Search .............................. 530/388.23, 350; 436/518, 529, 531, 69, 808, 501, 506; 526/72; 521/29; 435/13, 810, 975

[56] References Cited

U.S. PATENT DOCUMENTS

| | | |
|---|---|---|
| 4,613,665 | 9/1986 | Larm . |
| 4,707,471 | 11/1987 | Larm et al. . |
| 4,717,654 | 1/1988 | Savoca et al. . |
| 4,743,550 | 5/1988 | Ananthapadmanabhan et al. .. 435/220 |
| 4,795,745 | 1/1989 | Larm et al. . |
| 4,810,784 | 3/1989 | Larm . |
| 5,049,403 | 9/1991 | Larm et al. . |
| 5,213,898 | 5/1993 | Larm et al. . |
| 5,466,582 | 11/1995 | Amiral . |
| 5,618,917 | 4/1997 | Toback et al. ........................... 530/350 |
| 5,624,904 | 4/1997 | Krieger et al. ............................. 514/21 |

OTHER PUBLICATIONS

R. H. Aster, "The Immunologic Thrombocytopenias," *Platelet Immunobiology Molecular and Clinical Aspects* J.B. Lippincott Company, Philadelphia, PA, pp. 387 and 392, 1989.

J. Amiral, et al., "Antibodies to Macromolecular Platelet Factor 4–Heparin Complexes in Heparin–induced Thrombocytopenia: a Study of 44 Cases," *Thrombosis and Haemostasis* 73:21–28, 1995.

D. J. Christie, et al., "Drug–Antibody–Platelet Interaction in Quinine– and Quinidine–induced Thrombocytopenia," *J. Clin. Invest.* 70:989–998, 1982.

D. J. Christie, et al., "Fab–mediated Binding of Drug–dependent Antibodies to Platelets in Quinidine– and Quinine–induced Thrombocytopenia," *J. Clin. Invest.* 75:310–314, 1985.

M. N. Fukuda, et al., "Survival of Recombinant Erythropoietin in the Circulation: The Role of Carbohydrates," *Blood* 73(1):84–89, 1989.

M. Galli, et al., "Anti–Glycoprotein Ib/IX and IIb/IIIa Antibodies in Patients with Antiphospholipid Antibodies," *Thrombosis and Haemostasis* 71(5):571–575, 1994.

J. Hoffman, et al., "A new method for covalent coupling of heparin and other glycosaminoglycans to substances containing primary amino groups," *Carbohydrate Research* 117:328–331, 1983.

J.G. Kenton, et al., "Immunoglobin G from Patients with Heparin–induced Thrombocytopenia Binds to a Complex of Heparin and Platelet Factor 4," *Blood* 83(11):3232–3239, 1994.

L. LaFrance, et al., "Improved Heparin–Agarose: Higher Loading and Greater Stability," in *Sigma Com.*, pp. 2 and 3, 1995 (advertising communication from Sigma Chemical Co.).

O. Larm, et al., "Surface–immobilized heparin," in Heparin: Chemical and Biological Properties; Chemical Applications, D. A. Lane, U. Lindahl Eds., CRC Press, Boca Raton, Florida pp. 597–608, 1989.

O. Larm, et al., "Coupling of proteins and other amines to carbohydrate polymers via bromine oxidation and reductive animation," *Carbohydrate Research* 58:249–251, 1977.

R.J. Linhardt, et al., "Isolation and Characterization of Human Heparin," *Biochemistry* 31:12441–12445, 1992.

F.J. Morgan, et al., "Complete Covalent Structure of Human Platelet Factor 4," *Thrombos. Haemostas.* 42:1652–1660, 1979.

V.D. Nadkarni, et al., "Directional Immobilization of Heparin onto Beaded Supports," *Analytical Biochemistry* 222:59–67, 1994.

Pierce Derivatized Polystyrene Beads, Advertisement, 1995.

G.P. Visentin, et al., "Determinants on Heparin:PF4 Complexes Recognized by Antibodies Associated with Heparin–Induced Thrombocytopenia/Thrombosis (HITP)," *Blood* 4[10]:Suppl. 1, 1994.

(List continued on next page.)

*Primary Examiner*—Lila Feisee
*Assistant Examiner*—Eliane Lazar-Wesley
*Attorney, Agent, or Firm*—Quarles & Brady LLP

[57] ABSTRACT

A method of detecting heparin-induced antibodies to complete a diagnosis of heparin-induced thrombocytopenia HITP is disclosed. In one embodiment, this method comprises binding human platelet factor 4 to a linear, non-glycosaminoglycan polymer carrying negative charges distributed along the polymer chain, wherein the negative charge carried by the polymer is less than 10 Å from the polymer chain. In another embodiment, the negative charge is a strong negative charge. A complex having one or more epitopes recognizable by antibodies generated in a HITP immune response is formed. One then contacts blood plasma or serum from a human patient suspected of having HITP with the complex and analyzes the complex to determine if the HITP-related antibodies are present. In another embodiment of the invention, a kit for diagnosing HITP is disclosed.

7 Claims, 12 Drawing Sheets

OTHER PUBLICATIONS

G.P. Visentin, et al., "Characteristics of Quinine– and Quinidine–Induced Antibodies Specific for Platelet Glycoproteins IIb and IIIa," *Blood* 77(12:2668–2676, 1991.

G.P. Visentin, et al., "Antibodies Associated with Heparin–Induced Thrombocytopenia and Thrombosis (HITP) Recognize Platelet Factor 4 (FR) Bound to Heparin or Endothelial Cell Glycosaminoglycans (GAG)," *Blood* 82(Suppl. 1):163a, 1993 (abstract).

G.P. Visentin, et al., "Antibodies from Patients with Heparin–induced Thrombocytopenia/Thrombosis are Specific for Platelet Factor 4 Complexed with Heparin or Bound to Endothelial Cells," *J. Clin. Invest.* 93:81–88, 1994.

G. P. Visentin, et al., "A Prospective Study of the Formation of Antibodies Reactive with Heparin:PF4 Complexes in Patients Treated with Heparin," Abstract, 1994, ASH Meeting, Dec. 2–4, 1994.

X. Zhang, et al., "Crystal Structure of Recombinant Human Platelet Factor 4," *Biochemistry* 33:8361–8366, 1994.

J. Amiral, et al., "Platelet Factor 4 Complexed to Heparin Is the Target for Antibodies Generated in Heparin–Induced Thrombocytopenia," *Thromb. Haemo.* 68(1):95–96, 1992.

G. Arepally, et al., "Comparison of PF4/Heparin ELISA Assay With the $^{14}$C–Serotonin Release Assay in the Diagnosis of Heparin–induced Thrombocytopenia," *Coag. Trans. Med.* 104(6):648–654, 1995.

R.H. Aster, "Heparin–induced Thrombocytopenia and Thrombosis," *New Eng. J. Med.* 332(20):1374–1376, 1995.

B.H. Chong, et al., "The Clinical Usefulness of the Platelet Aggregation Test for the Diagnosis of Heparin–induced Thrombocytopenia," *Thromb. Haemo.* 69(4):344–350, 1993.

H.C. Godal, "Heparin–induced Thrombocytopenia," *Heparin: Chemical and Biological Properties, Clinical Applications*, CRC Press, Inc., Boca Raton, Florida, pp. 533–543, 1989.

A. Greinacher, et al., "Heparin–Associated Thrombocytopenia: Isolation of the Antibody and Characterization of a Multimolecular PF4–Heparin Complex as the Major Antigen," *Endo. Cell Cult.* pp. 247–251, 1993.

A. Greinacher, et al., "Laboratory diagnosis of heparin–associated thrombocytopenia and comparison of platelet aggregation test, heparin–induced platelet activation test, and platelet factor 4/heparin enzyme–linked immunosorbent assay," *Transfusion* 34(5):381–382, 1994.

A. Greinacher, et al., "Characterization of the Structural Requirements for a Carbohydrate Based Anticoagulant with a Reduced Risk of Inducing the Immunological Type of Heparin–associated Thrombocytopenia," *Thromb. Haemo.* 74(3):886–892, 1995.

A. Greinacher, "Antigen Generation in Heparin–Associated Thrombocytopenia: The Nonimmunologic Type and the Immunologic Type Are Closely Linked in Their Pathogenesis," *Sem. Thromb. Hemo.* 21(1):106–116, 1995.

J.G. Kelton, et al., "Heparin–Induced Thrombocytopenia: Laboratory Studies," *Blood* 72(3):925–930, 1988.

J.G. Kelton, et al., "Diagnosis of Heparin–induced Thrombocytopenia," *Am. J. Clin. Path.* 104(6):611–613, 1995.

J.G. Kelton, "Heparin–induced Thrombocytopenia: What the Serologists have Taught us," *J. Lab. Clin. Med.* 128(4):346–348, 1996.

M. Maccarana and U. Lindahl, "Mode of Interaction between Platelet Factor 4 and Heparin," *Glycobiology* 3(3):271–277, 1993.

K. Mayo, et al., "Heparin Binding to Platelet Factor–4," *Biochem. J.* 312:357–365, 1995.

D. Sheridan, et al., "A Diagnostic Test for Heparin–induced Thrombocytopenia," *Blood* 67(1):27–30, 1986.

J.A. Stuckey, et al., "A Model of the Platelet Factor 4 Complex with Heparin," *Proteins* 14:277–287, 1992.

G.P. Visentin, et al., "Antibodies from Patients with Heparin–induced Thrombocytopenia/Thrombosis are Specific for Platelet Factor 4 Complexed with Heparin or Bound to Endothelial Cells," *J. Clin. Invest.* 93:81–88, 1994.

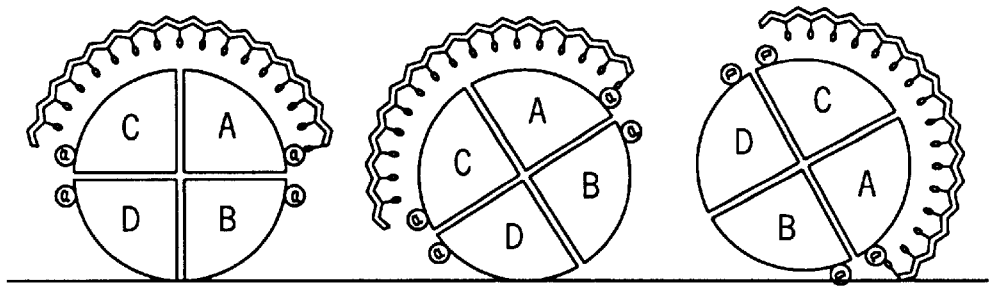
FIG. 1B
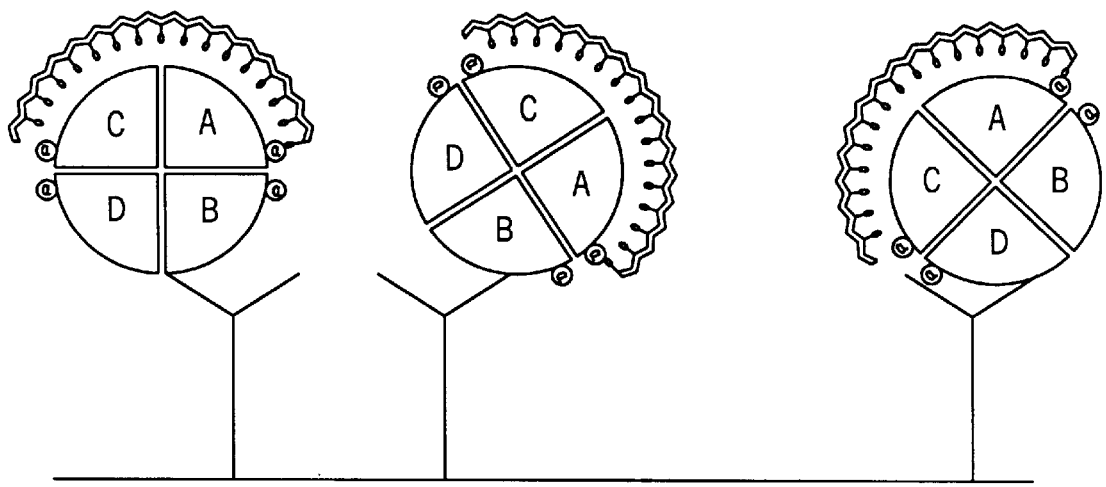
FIG. 1C
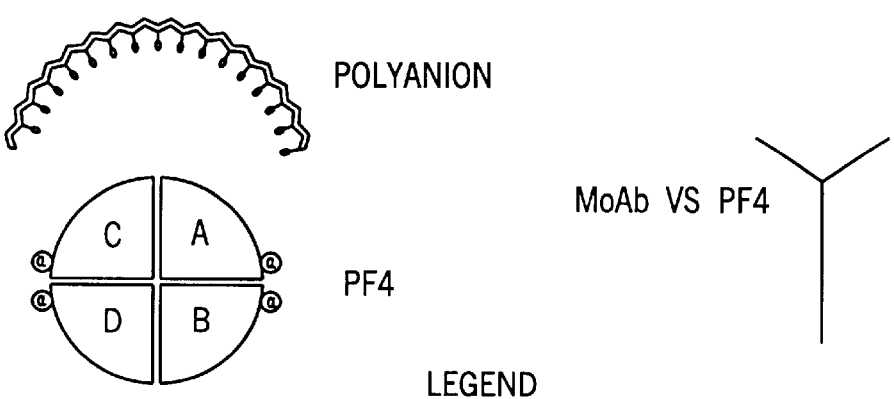
LEGEND

```
SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70
```

METHOD OF DETECTING HEPARIN-INDUCED THROMBOCYTOPENIA

CROSS-REFERENCE TO RELATED APPLICATIONS

This Application claims benefit of Provisional Application No. 60/012,445 filed Feb. 28, 1996.

BACKGROUND OF THE INVENTION

Thrombocytopenia (low blood platelet levels) is most often caused either by defective platelet production or excessive platelet destruction. Defective platelet production is a common manifestation of many toxic, nutritional, and neoplastic disturbances of the bone marrow. Increased peripheral destruction of platelets is characterized by shortened platelet survival and increased proliferation of bone marrow megakaryocytes in an effort to compensate for the low platelet levels. Frequently, this process is immunologically mediated.

Certain drugs and their metabolites induce antibodies in some individuals which can cause immune platelet destruction. Implicated drugs include quinidine and quinine (stereoisomers of each other), sulfonamide antibiotics and many others (R. H. Aster, in *Platelet Immunobiology: Molecular and Clinical Aspects.* T. J. Kunicki and J. N. George eds., Lippincott, Philadelphia, pp. 387–435, 1989; N. R. Shulman, et al., "Platelet Immunology" in *Hemostasis and Thrombosis: Basic Principles and Clinical Practice.* R. W. Culman, J. Hirsh, V. J. Marder, E. W. Salzman, eds. Lippincott, Philadelphia, 2nd ed., pp. 452–529, 1989). A few of these drugs, such as penicillin, appear to bind covalently to platelet proteins and stimulate the formation of antibodies specific for the drug-protein complex (hapten-dependent antibodies) (D. J. Salamon, et al., *Transfusion* 24:395, 1984). More often, however, the sensitizing drug or one of its metabolites induces the formation of antibody by an unknown mechanism (Aster, supra, 1989; A. Salama, et al., *Sem. Hematol.* 29:54–63, 1992). The resulting antibodies bind to platelets only in the presence of drug to cause platelet destruction. Evidence obtained by the Applicants (D. J. Christie, et al., *J. Clin. Invest.* 75:310, 1985; D. J. Christie, et al., *J. Clin. Invest.* 70:989, 1982) and others (C. Mueller-Eckhardt, et al., *Trans. Med. Rev.* 4:69, 1990; A. Salama, et al., *Semin. Hematol.* 29:54, 1992) indicates that in such cases, the drug binds non-covalently and reversibly to selected platelet membrane proteins to induce conformational changes or form compound epitopes that are recognized by the antibodies. Drug-dependent binding of the antibodies to platelets causes the platelets to be destroyed. In the several forms of drug-induced immune thrombocytopenia, platelet counts are often very low and bleeding complications are frequently severe.

A third type of drug-induced thrombocytopenia (heparin-induced thrombocytopenia or HITP) occurs in patients treated with heparin to prevent or treat thrombosis. Heparin is a family of polysaccharide species consisting of chains made up of alternating, 1–4 linked and variously sulfated residues of glucuronic acid or iduronic acid and D-glucosamine. (B. Casu, "Methods of structural analysis" in *Heparin: Chemical and Biological Properties, Clinical Applications,* D. A. Lane and U. Lindahl, eds. CRC Press, Inc. Boca Raton, Fla., 1989, pp. 25–49.) In man and animal species, heparin is normally found in storage granules of mast cells (tissue basophils) (L. Enerback, "The mast cell system." In *Heparin: Chemical and biological properties, clinical applications,* D. A. Lane and U. Lindahl eds. CRC press, Inc., Boca Raton, Fla., pp. 97–114, 1989). Heparin-like molecules, such as heparan sulfate and chondroitin sulfate are expressed on the surface of endothelial cells that coat the luminal surface of blood vessels and in other tissues where they are coupled to a protein backbone (syndecan) to form a class of molecules known as proteoglycans (Ihrcke, et al., *Immunology Today* 14:500–505, 1993). The heparin-like residues on endothelial cell proteoglycans are thought to provide one means by which abnormal clotting is prevented, allowing the circulating blood to remain in a fluid state (J. A. Marcum, et al., "The biochemistry, cell biology, and pathophysiology of anti-coagulantly active heparin-like molecules of the vessel wall" in *Heparin: Clinical and Biological Properties, Clinical Applications.* D. A. Lane and U. Lindahl eds., CRC Press, Inc., Boca Raton, Fla., pp. 275–294, 1989). Heparin acts as an anticoagulant by binding to a co-factor protein, antithrombin III, in such a way as to enable this protein to inhibit certain activated clotting factors, especially activated Factor X (Xa) and thrombin (IIa) (I. Bjork, et al., "Molecular mechanisms of the accelerating effect of heparin on the reactions between antithrombin and clotting proteases" in *Heparin: Chemical and Biological Properties, Clinical Applications,* D. A. Lane and U. Lindahl eds., CRC Press, Inc., Boca Raton, Fla., pp. 229–255, 1989). Heparin of bovine origin appears to be more likely to cause HITP than heparin of porcine origin (W. R. Bell, et al., *N. Engl. J. Med.* 33:902, 1980).

Thrombocytopenia in patients with HITP is usually not severe enough to result in bleeding. However, patients with this condition often experience thrombosis in major arteries and/or veins which can be fatal or cause the loss of a limb or a stroke. After discontinuation of heparin in patients with HITP, the platelet levels generally return to normal.

HITP appears to be caused by IgG, IgM or IgA antibodies that develop after five or more days of heparin therapy (G. P. Visentin, et al., *J. Clin. Invest.* 93:81–88, 1994 and J. S. Suh, et al., *Am J. Hematol,* in press, 1995). These antibodies differ from those associated with other forms of drug-induced thrombocytopenia in that, in the presence of optimal concentrations of heparin, they activate blood platelets, causing the platelets to release the contents of their storage granules and to undergo membrane changes that create sites for the binding of a coagulation factor, fibrinogen, normally present in plasma (B. H. Chong, et al., *Br. J. Haematol.* 64:347, 1986). The Applicants and others have shown that antibodies associated with HITP are specific for complexes of heparin and platelet factor 4 (PF4), a basic heparin-binding protein normally present in platelet storage granules (Visentin, et al., 1994, supra; Amiral, et al., *Thromb. Haemostasis* 68:95–96, 1992).

On the basis of findings made in their laboratory, the Applicants recently proposed the following new hypothesis to explain the development of thrombocytopenia and thrombosis in patients sensitive to heparin (Adapted from G. P. Visentin, et al. *J. Clin. Invest.* 93:81–88, 1994): In a patient with IgG antibodies specific for heparin/PF4 complexes who is treated with heparin, a) minimal activation of circulating platelets by heparin alone (C. Eika, *Scand. J. Hematol.* 9:480, 1972) or by immune complexes consisting of heparin, PF4, and IgG, leads to release of PF4 from platelet alpha-granules in a complex with chondroitin sulfate (S. Huang, et al., *J. Biol. Chem.* 257:11546, 1982); b) circulating heparin displaces the chondroitin sulfate to form heparin/PF4 complexes (R. Handin, et al., *J. Biol. Chem.* 251:4273, 1980); c) antibodies bind to heparin/PF4 to form immune complexes in close proximity to the platelet surface; d) these complexes bind to platelet Fc receptors, activate platelets, and release more PF4; e) the additional PF4 released reacts with heparin and IgG to form new immune complexes, promoting further platelet activation and causing thrombocytopenia; and f) PF4 released from platelets in excess of the amount that can be neutralized by available heparin binds to heparan sulfate on endothelial cells to create targets for IgG, IgA, or IgM antibodies leading to antibody-mediated endothelial injury and a predilection to thrombosis or disseminated intravascular coagulation. IgM antibodies, because of their greater capacity for complement activation, may be more destructive to endothelial cells than those of the IgG or IgA classes.

Because of the morbidity and mortality associated with HITP, it is important that the diagnosis be made quickly and accurately in a patient who develops thrombocytopenia while receiving heparin. Failure to make a diagnosis in such patients can lead to continuation of heparin therapy and fatal outcome. Assays used to diagnose other forms of drug-induced thrombocytopenia, i.e., binding of IgG or IgM antibodies to normal target platelets in the presence of drug (R. H. Aster, *The Immunologic Thrombocytopenias in Platelet Immunology.* T. J. Kunicki and J. N. George eds., Lippincott, Philadelphia, Pa., pp. 387–435, 1989) are not useful in detecting antibodies associated with HITP (G. P. Visentin, 1994, supra; H. C. Godal, "Heparin-induced thrombocytopenia" in *Heparin: Chemical and Biological Properties, Clinical Applications,* D. A. Lane and U. Lindahl eds., CRC Press, Inc., Boca Raton, Fla., pp. 533–548, 1989).

Accordingly, diagnostic techniques have been developed that make use of the ability of HITP-associated antibodies to activate platelets in the presence of optimum concentrations of heparin. One such test is the platelet aggregation test which is done by mixing the following reagents together in a test tube: normal platelet-rich plasma anti-coagulated with citrate, heparin at a concentration of about one unit per ml, and plasma or serum from the patient suspected of having HITP. The mixture is incubated at 37° C. and stirred. In a positive reaction, the antibody activates the platelets, causing the platelets to aggregate. The extent of aggregation is measured by an increase in light transmission through the mixture (J. G. Kelton, et al., *Blood* 72:925–930, 1988 and B. H. Chong *Thromb Haemostasis* 69:344–350, 1993). The assay is then repeated using a much higher concentration of heparin, e.g., 100 units per ml. Aggregation with the lower dose of heparin and lack of aggregation with the higher dose constitutes a positive test for HITP antibody.

A second and more sensitive test, also dependent on the ability of HITP antibodies to activate platelets, is the $^{14}$C-serotonin release test (D. Sheridan, et al., *Blood* 67:27–30, 1986). In this assay, washed, normal donor platelets radiolabeled with $^{14}$C-serotonin are suspended in buffer and test serum. Heparin at a concentration of about 0.1 units per ml is then added and the mixture is agitated for about 30 minutes. In a positive test, $^{14}$C-serotonin is released from the platelets by virtue of their being activated by the HITP antibody (Sheridan, 1986, supra). As with the aggregation test, specificity of the reaction is confirmed by showing that $^{14}$C-serotonin release is inhibited by a high dose of heparin, e.g., 100 units per ml.

Another disclosed method is an assay for heparin-induced IgG antibodies based on their reaction with immobilized complexes of heparin and platelet factor 4 (PF4) (see Amiral, et al., *Thromb. Haemostasis* 68:95–96, 1992). PF4 is a protein component of platelet alpha granules which is positively charged at neutral pH and is known to be capable of binding to and inhibiting the function of heparin. PF4 for use in the assay can be obtained by cleavage or lysis of normal platelets (see PCT Application WO96/02833, 1992).

PF4 belongs to a family of cytokines called "intercrines" or "chemokines" involved in the mediation of certain immune reactions and other activities (see Masushima, et al., *Cytokines* 1:2–13, 1989). PF4 has high affinity for heparin (see Handin, et al., *J. Biol. Chem.* 251:4273–4282, 1976) and is able to neutralize the anticoagulant properties of heparin (see Lane, et al., *Biochem. J.* 218:725–732, 1984, Machalski, et al., *Br. J. Haematol.* 38:561, 1978).

The heparin/PF4 assay described by Amiral (supra) is more convenient than the platelet aggregation test and the serotonin release test, which depend on activation of fresh platelets. However, discrepancies were observed when comparing results obtained with the heparin/PF4 assay with those obtained in a platelet aggregation test (see Greinacher, et al., *Transfusion* 34:381–385, 1994).

The assays and detection methods described above all relate to the formation and detection of heparin/PF4 or glycosaminoglycan/PF4 complexes by heparin-induced antibodies. Needed in the art is a method of detecting antibodies generated in a HITP immune response by use of a complex that does not contain heparin or other glycosaminoglycans.

BRIEF SUMMARY OF THE INVENTION

The present invention provides a method for detecting heparin-induced antibodies to complete a diagnosis of HITP. The method begins by attaching a complex comprising a linear, negatively charged, non-glycosaminoglycan polymer and PF4, preferably a polyvinyl sulfate/PF4 complex, covalently or by passive adsorption to a solid support. In one embodiment, the negative charge carried by the polymer is less than 10 Å, preferably less than 6 Å, from the polymer chain. In another embodiment, the negative charge is a strong negative charge at neutral pH.

Blood plasma or serum from a patient suspected of having HITP is then exposed to the complex, and the complex is then analyzed to determine whether HITP-related antibodies have become associated with it. Preferably, the blood plasma or serum is from a human patient.

In a preferable form of the present invention the polymer is not a carbohydrate.

In another form of the present invention, the spacing of the negative charges on the polymer is less than 10 Å, preferably less than 6 Å. Most preferably, the average distance between negative charges is 4 angstroms (±1 angstrom).

In another preferable form of the present invention, the polymer has a molecular weight between 2000 and 6000 daltons. In a most preferred form of the present invention, the median molecular weight of the polymer is 5000 Daltons.

In another preferable embodiment, the polymer comprises at least 10 subunits, preferably between 15 and 50 subunits, each bearing a negative charge.

In one preferable embodiment of the method, analyzing the complex consists of measuring the quantity of a detectable label and then measuring the product of the enzymatic reaction. The method further consists of contacting the complex attached to the solid support with an immunological component that binds to human antibody. The immunological component is attached to the detectable label.

In a preferred embodiment, the detectable label is alkaline phosphatase and the quantity of label is measured by adding a substrate to react with the label. Preferably, the substrate used is p-nitrophenyl phosphate (PNPP).

The platelet factor 4 (PF4) is preferably selected from the group consisting of native PF4, recombinant PF4, and PF4 created through chemical protein synthesis techniques. We refer to PF4 created via chemical protein synthesis techniques as "synthetic" PF4.

Preferably, the PF4 is human PF4 or synthetic peptides containing amino acids found in human PF4 which form epitopes recognized by HITP antibodies when complexed with polyvinyl sulfate for the present invention. In a preferred embodiment, PF4 is obtained by pooling platelets from normal whole human blood and releasing PF4 by adding thrombin-receptor activating peptide (TRAP) T. K. Vu, et al., Nature 353:674–677, 1991 and then purifying the released PF4 to homogeneity (Visentin, et al., supra, 1994).

A kit for diagnosing HITP is provided. This kit comprises a solid support preferably prepared by attaching the polymer/PF4 complex covalently or passively to the solid support or attaching polyvinyl sulfate to the solid support and then linking PF4 to the polymer to form a complex having an epitope recognizable by antibodies generated in an HITP immune response. The kit typically includes a receptacle containing a chemical label for detecting an amount of antibody present as well as a receptacle containing a substrate of the chemical label which reacts with the chemical label to produce a measurable signal. Instructions for use are typically included.

Preferably, the chemical label in the kit comprises a component selected from the group consisting of an anti-human IgG/enzyme complex, an anti-human IgM/enzyme complex or an anti-human IgA/enzyme complex or a polyvalent probe that recognizes all three immunoglobulins (IgG, IgM, IgA). Preferably, a stabilizing agent is added to the solid support to preserve the ability of the complex to bind with antibody over a period of time and to lower non-specific binding of immunoglobulins to the solid support, thus reducing background.

It is an advantage of the present invention that an HITP assay may be performed with polyvinyl sulfate/PF4 complexes or complexes comprising PF4 and any one of many linear, negatively charged, non-glycosaminoglycan polymers preferably with a series of negative charges carried by the polymer and located at a distance less than 10 Å, preferably less than 6 Å, from the polymer chain backbone and most preferably with the polymer carrying a series of strong negative charges spaced 4 Å (±1 Å) apart.

It is another advantage of the present invention that complexes may be formed over at least a 10,000-fold range of polymer concentration when using low molecular weight polyvinyl sulfate (median MW about 5,000, preferable range about 2,000–6,000), keeping the concentration of PF4 constant. This advantage is in sharp contrast to the limited range of heparin/PF4 complexes that are suitable for HITP antibody detection. For example, Visentin, et al., supra, 1994 showed that with heparin at a concentration of 0.3 units per ml, good antibody binding was observed with PF4 at 10 µg/ml. However, the binding was completely lost when PF4 was increased 2.5-fold to 25 µg/ml and was greatly diminished when PF4 concentration was reduced by 50% to 5 µg/ml. With certain batches of heparin, the ratio of heparin to PF4 used to make complexes that are suitable for antibody detection was even more restricted.

In contrast, Example 3, below, shows that when using PF4 at a concentration of 10 µg/ml, the polyvinyl sulfate concentration can be varied from 7.5 µg/ml to 1500 µg/ml without affecting the ability of the resulting polyvinyl sulfate/heparin complexes to bind to HITP antibody. Even with a 10,000-fold range in concentration (polyvinyl sulfate 0.15 to 1500 µg/ml) positive reactions were obtained, although the OD values were lower at the extreme polyvinyl sulfate concentrations. It is apparent that the ratio of the two reactants is much less critical than with heparin.

It is another advantage of the present invention that the repeating subunits are identical to one another, thus assuring regular spacing of the anionic side chain. In contrast, heparin consists of several types of repeated disaccharides which can be variously substituted by sulfate and acetyl amine.

It is another advantage of the present invention that an HITP assay may be performed with a compound that is less costly than heparin. For example, polyvinyl sulfate is a synthetic compound that can be readily produced in industrial quantities. In contrast, heparin is a pharmaceutical that must be isolated from porcine intestinal mucosa or beef lung in a costly and complex purification process.

It is another advantage of the present invention that an HITP assay is provided wherein the complexes are not sensitive to the action of enzymes, such as heparinases, that inactivate heparin preparations. Additionally, heparin tends to degrade spontaneously when it is stored in liquid state for more than 1 or 2 years. Polyvinyl sulfate, in contrast, is resistant to heparinases and stable indefinitely.

It is another advantage of the present invention that complexes, such as polyvinyl sulfate (PVS):PF4 complexes, are less susceptible to disruption by added heparin than heparin:PF4 complexes. Thus, residual heparin in test serum is less likely to obscure a positive reaction.

It is yet another advantage of the present invention that each stage of the testing can be as short as 30 minutes because incubations can be carried out at 37° C. In contrast, heparin/PF4 complexes are unstable at 37° C. and must be incubated at room temperature for one to two hours to obtain satisfactory reactions.

Other objects, features and advantages of the present invention will become apparent from the following detailed description and examples. The specific examples, while indicating preferred embodiments of the invention, are given by way of illustration only, since various changes and modifications within the spirit and scope of the invention will become apparent to those skilled in the art.

BRIEF DESCRIPTION OF THE SEVERAL VIEWS OF THE DRAWINGS

FIGS. 1A–C is a diagram of polymer attachment to PF4. FIG. 1A schematically depicts the typical anionic polymer and its interaction with the positively charged PF4 molecule. FIG. 1B depicts immobilization of polyanion-PF4 complexes directly on a polystyrene microtiter plate, and FIG. 1C depicts immobilization of polyanion/PF4 complexes using an immobilized monoclonal antibody specific for PF4.

DETAILED DESCRIPTION OF THE INVENTION

A. In General

Figure 1A:
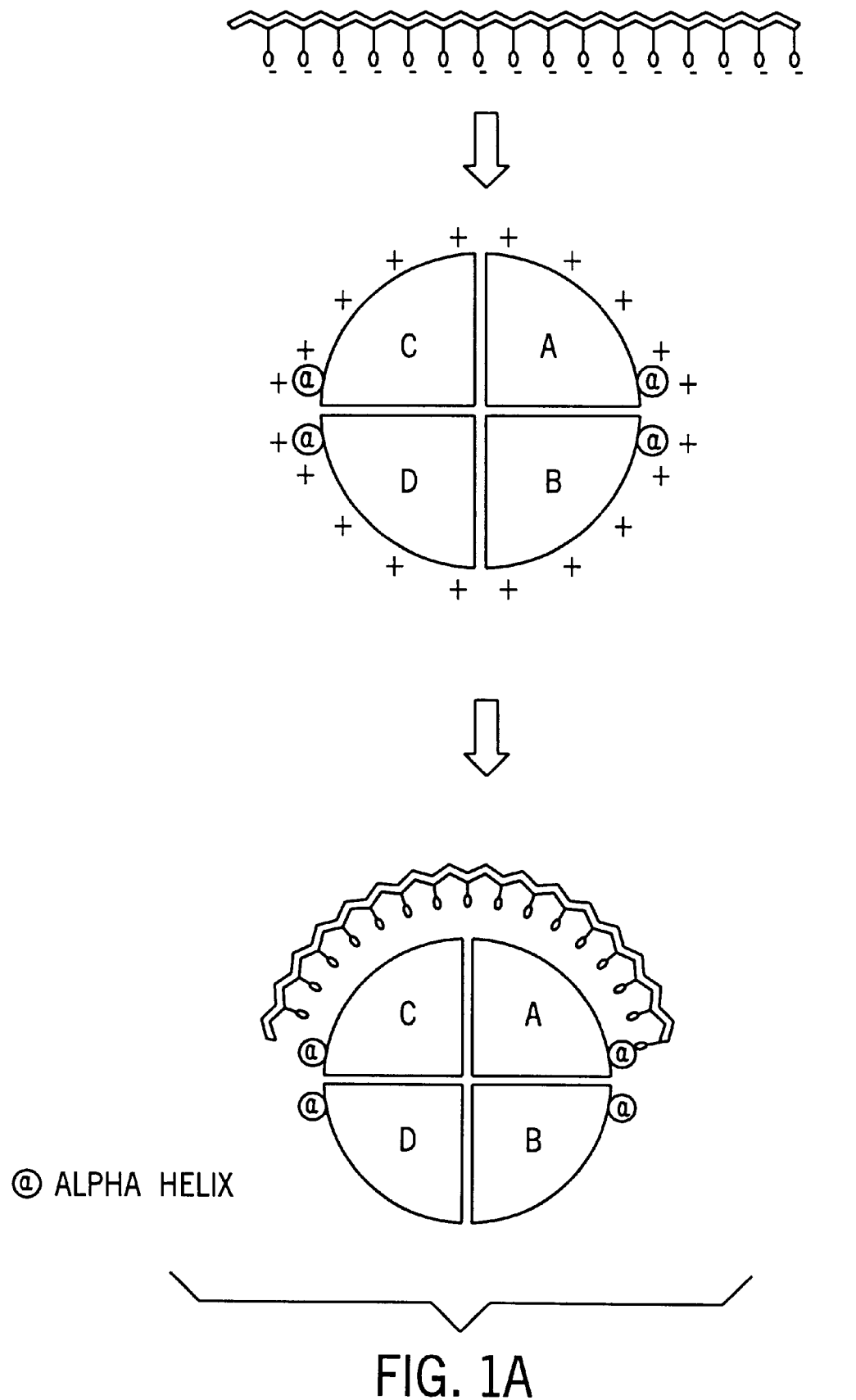

The present invention relates to our discovery that platelet-activating, heparin-induced antibodies specifically recognize PF4/polymer complexes. The polymers of the present invention are preferably linear, strongly negatively charged non-glycosaminoglycan molecules that carry the negative charge within 6 Å from the polymer chain backbone. In the present invention, the complexes are preferably immobilized on a solid support, such as a microtiter plate well, and detected, preferably using colorimetric techniques. Thus, the present invention provides a way of assaying a patient's blood plasma or serum sample for the presence of antibodies developed by patients treated with heparin that avoids disadvantages of the prior art, heparin-containing systems.

The present invention provides a new approach for detection of HITP antibodies which typically involves: 1) incubation of a negatively charged polymer, such as polyvinyl sulfate, with PF4 to form polymer/PF4 complexes, 2) the attachment of synthetic polymer/PF4 complexes to the surface of a solid support by covalent linkage, passive adsorption, or binding to a monoclonal antibody specific for PF4, 3) preferably, the addition of a stabilizing agent, 4) addition of serum or plasma from a patient with HITP-generated antibody, and 5) detection of antibody bound to the target synthetic polymer complexes with a suitable antibody-specific probe.

B. Attachment of the polymer/PF4 complex to a solid support

The description below will describe the attachment process with reference to low molecular weight polyvinyl sulfate (2,000–6,000, median 5,000). We envision that other polymers, especially the polyanions presented below in the Examples, would be equally suitable. However, polyvinyl sulfate or polyvinyl sulfonic acid are referenced for simplicity and clarity.

1. Attachment Process

A prerequisite for detection of HITP antibodies by the method of the present invention is the availability of target complexes consisting of human PF4 complexed with polyvinyl sulfate. Polyvinyl sulfate/PF4 complexes or polyvinyl sulfonic acid/PF4 complexes can be immobilized on a solid surface by several different methods. One advantage of the present method is that the concentration of polyvinyl sulfate or polyvinyl sulfonic acid relative to PF4 may vary up to 10,000-fold and still achieve a polymer/PF4 complex that reacts with antibody. This finding is in contrast to the use of heparin/PF4 complexes in an HITP assay. Visentin, et al. (*J. Clin. Invest.* 93:81–88, 1994) demonstrated that using fresh commercial heparin preparations, only heparin/PF4 complexes formed at a certain critical ratio of the reactants are capable of binding HITP antibodies efficiently. At a fixed concentration of PF4, no more than a 10-fold range of heparin concentration can be tolerated without marked decrease in antibody binding efficiency. Moreover, the optimal ratio of heparin to PF4 for formation of complexes that bind antibody is not the same for different lots of heparin (Visentin, et al., *J Clin Invest* 93:81–88, 1994).

The preferred method of creating a polyvinyl sulfate/PF4 complex is described below in Examples 3 and 4. In Example 3, concentrations of polyvinyl sulfate ranging from 0.15–1500 µg/ml were mixed with 10 µg/ml of PF4 in PBS (phosphate buffered saline, pH 7.2). The experiment described in Example 3 showed that this entire range of polyvinyl sulfate concentration was suitable. Concentrations of between 7.5 µg/ml and 750 µg/ml of polyvinyl sulfate per 10 µg/ml PF4 were especially preferred. Fifty microliters aliquots of polyvinyl sulfate/PF4 complex are then added to polystyrene microtiter plates and incubated overnight (typically at 4–16 hours at 4–8° C.). The microtiter plates are then typically washed 3× with PBS-0.05% Tween 20 (Tw) and blocked for 1 hour at room temperature with PBS-Tw-1% bovine serum albumin.

Fifty microliters of plasma diluted 1:50 or 1:100 in PBS are typically added to wells of microtiter plate to be tested.

FIG. 1A depicts a typical anionic polymer, consisting in this case of 16 subunits totalling about 70 angstroms in length that binds to a ring of positive charges on PF4 (J. A. Stuckey et al., Proteins 14:277–87, 1992), causing distortion of the PF4 molecule and creating "neoepitopes" on PF4 for which HITP antibodies are specific (G. P. Visentin et al., Proceedings XVIth Congress Int. Soc. on Thrombosis and Haemostasis, in press). This figure is intended for illustration only—the exact regions on PF4 to which the anionic polymer binds and the details of the resulting structural changes in PF4 are not yet fully defined.

Approaches for attaching polyanion/PF4 complexes to solid supports are shown schematically in FIGS. 1B and C.

FIG. 1B describes immobilization of polyanion-PF4 complexes directly on a polystyrene microtiter plate. FIG. 1C describes immobilization of polyanion-PF4 complexes using an immobilized monoclonal antibody specific for PF4. To avoid competition with the human antibodies to be detected, the monoclonal antibody must bind to a region of PF4 known not to be recognized by the human antibodies.

To practice the method of the present invention, one would preferably attach a polyvinyl sulfate/PF4 complex to a solid support, such as a microtiter plate well or bead. Suitable polymers other than polyvinyl sulfate are discussed below.

The solid support must be capable of binding the polyvinyl sulfate/PF4 complex. Examples of such solid supports include plates or cups made of hydrocarbon polymers such as polystyrene, polyethylene and polybutylene.

2. Suitable Polymer Molecules

A suitable polymer for the present invention is linear and is not a glycosaminoglycan. The polymer carries multiple negative charges distributed along its length, preferably at every subunit. The polymer is not a carbohydrate and is synthetic.

Figure 11:
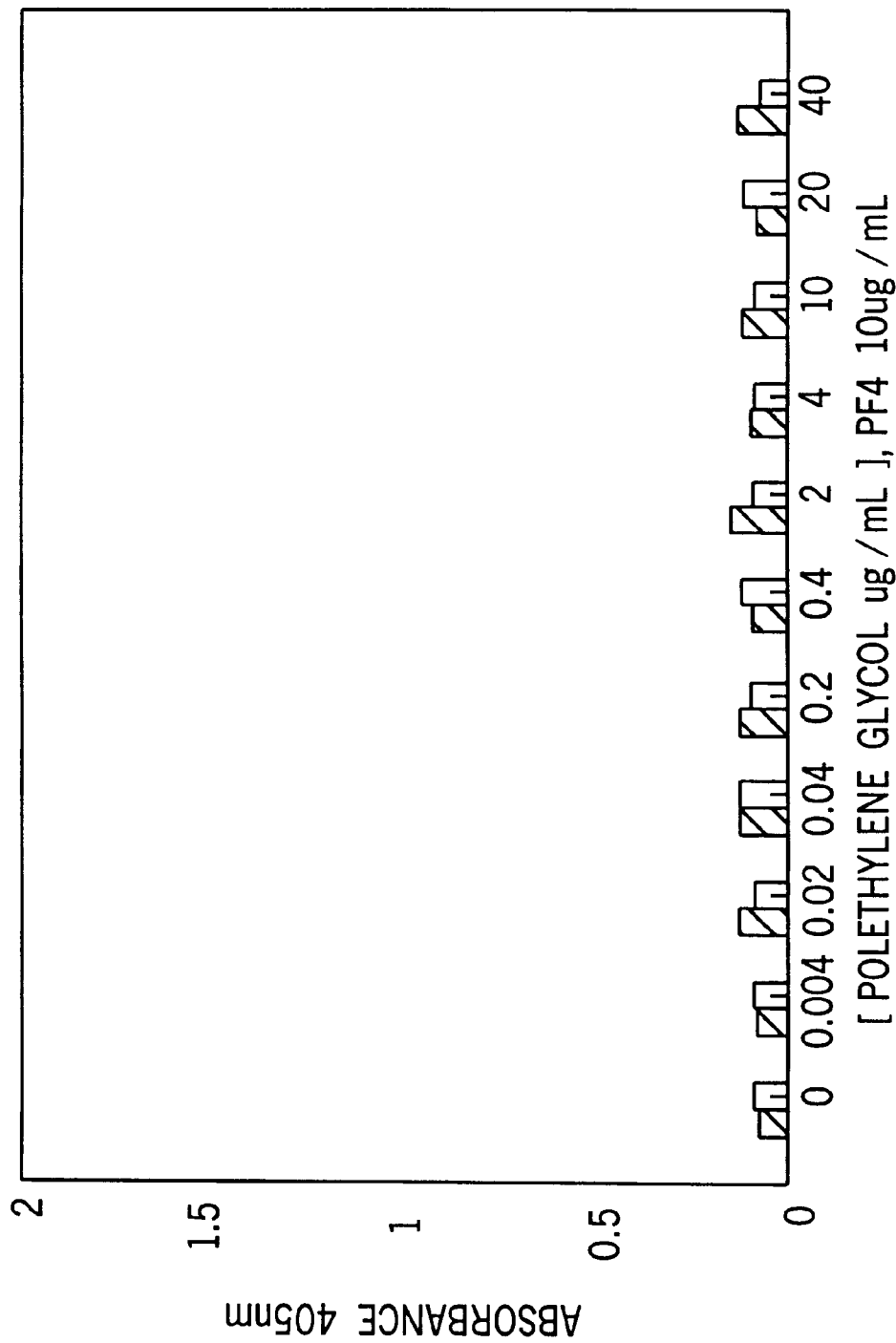
FIG. 11 is a bar graph comparing optical density obtained after a patient sample (dark bars) and a normal sample (open bars) were added to immobilized polyethylene glycol/PF4 complexes prepared by mixing PF4 (10 µg/ml) with different amounts of polyethylene glycol.

A polymer of equal length, such as polyethylene glycol, that does not carry negative charges is not a suitable polymer for the present invention (FIG. 11).

In one embodiment of the present invention, a suitable polymer for the present invention carries the negative charge within 6 Å from the polymer backbone. Thus, a negatively charged polymer such as poly-D-glutamic acid, in which the negative charge is attached to the polymer backbone by a spacer molecule, is not a suitable negatively charged polymer of the present invention.

A polymer containing a strong negative charge is preferable for the present invention. By "strong" negative charge, we mean the charge at neutral pH comparable to that of a polymer substituted with multiple sulfate, sulfonate, phosphate or phosphonate groups. An example of a polymer that does not contain a strong negative charge is poly-D-glutamic acid, which carries its charge on a carboxyl group.

The fractionated size of the polymer is also significant in terms of the success of the present invention. We have found that a polymer size of 2–6,000 daltons is preferred for the present invention. Larger polymers can be used but are less suitable because complexes of polymer/PF4 that bind HITP antibodies effectively are formed over a more limited range of polymer concentration.

A polymer of greater than 10 subunits, preferably between 20 and 60 subunits, is preferable.

A polymer with regularly spaced negative charges, preferably less than 10 Å apart and most preferably less than 6 Å apart, is preferred. However, we envision that the polymer need not always contain a regularly spaced negative charge and that polymers with substituted or removed negative charges in some locations would also be suitable for the present invention.

In polyvinyl sulfate (PVS), the sulfate radicals are regularly spaced at intervals of 4.4 angstroms (if the chain is considered to be "taut") or 3.6 angstroms (if three adjacent carbon atoms assume an angle of about 109° as is true of a hydrocarbon chain floating freely in solution). Therefore, a desirable polyanion for purposes of this invention is a linear polymer carrying strong negative charges (e.g., phosphate or sulfate) along its length at intervals of approximately 4 angstroms. Polymers containing more densely arranged negative charges might work (but would be hard to synthesize), and polymers containing negative charges that are more than 40 angstroms apart probably will not work very well.

We envision that polyvinyl sulfate/PF4 complexes are preferably attached to solid support according to the method of the present invention. By "polyvinyl sulfate" we mean a molecule of the formula $-[CH_2-CH-(OSO_3\ K)-]_n-$ wherein n preferably ranges from 20 to 60. (Salts of sodium and other cations would also be satisfactory.) In our Examples below, the polyvinyl sulfate had a molecular weight of approximately 5,000 D (or 40 subunits).

We also envision that one would find other polymers, preferably synthetic sulfated and phosphorylated polyanions, suitable for use in the present invention. Specifically, the Examples below demonstrate the efficacy of polyvinyl sulfonic acid, polystyrene sulfonate, polyanetholesulfonic acid, polyvinyl phosphoric acid, and polyvinylphosphonic acid.

C. Platelet Factor 4

In its natural state, human platelet factor 4 is a tetramer with a molecular weight of approximately 32,000 daltons (see Ryo, et al., *Thromb. Res.* 17:465–652, 1980; Zucker, et al., *Proc. Soc. Exp. Biol. Med.* 198:693–702, 1991, for a full description of PF4). The PF4 used in the method may be PF4 derived from human platelets, recombinant human PF4 or human PF4 manufactured by standard peptide synthesis. SEQ ID NO:1 is the amino acid sequence of human PF4 (from Poncz, et al., *Blood* 69:219–223, 1987.

The PF4 derived from platelets is typically obtained by pooling platelets from whole blood donors in a suspension and releasing PF4 by adding thrombin-receptor activating peptide (TRAP 11). (T. K. H. Vu, et al., *Cell* 64:1057–1068, 1991; T. K. H. Vu, et al., *Nature* 353:674–677, 1991.) This method causes the release of platelet alpha granule constituents, including PF4, without release of other proteins, providing a significant purification of PF4 in only one step. This procedure is described in detail in Example 2.

In place of whole PF4, a peptide fragment or fragments having amino acid sequences found in human PF4 may be substituted. Furthermore, a peptide capable of binding to a glycosaminoglycan (GAG) such as heparin to form an epitope recognized by antibodies generated in an HITP immune response may be substituted for PF4 in the methods described.

To determine whether a candidate PF4 fragment or a peptide is suitable for the present invention, one would perform a comparison between the candidate peptide and native PF4. An efficacy of binding HITP-generated antibodies of at least 50% that of native PF4 would indicate that the fragment was suitable for the present invention.

D. Patient Samples

Blood plasma or serum is obtained from a patient suspected of having HITP. Preferably, small amounts, such as 0.2 ml, are needed for a test reaction.

It is an advantage of the method of the present invention that either serum or plasma can be used as the source of HITP antibody without concern for its PF4 and heparin content. In the method of the present invention, polyvinyl sulfate molecules (or other polyanions) are complexed to platelet factor 4 to provide targets for HITP antibody detection.

Small amounts of residual heparin present in serum or plasma to be tested for HITP antibodies can interfere with antibody detection by coating exposed regions of PF4 to block antibody binding sites. Because samples for testing are often obtained from patients who recently received heparin, it is not uncommon for residual heparin to be present. When patient samples are used at high concentrations (1:10 dilution) it is preferable that this residual heparin be removed by absorption with Ecteola cellulose or a similar agent to achieve maximum sensitivity for antibody detection. The blood plasma may be absorbed with Ecteola cellulose (epichlorohydrin triethanolamine cellulose) to remove traces of residual heparin (A. R. Thompson, et al., *J. Lab. Clin. Med.* 88:922–929, 1976, G. P. Visentin, et al., 1994, supra).

The sample is preferably diluted to a ratio of 1:50–1:100 V/V or more before being added to each of the microtiter plate wells. The plates are typically incubated at 37° for 30 minutes or room temperature for 1–2 hours and then washed with PBS containing 0.05% TWEEN 20 (PBS-Tw) to remove unbound antibody.

E. Quantitative Determination

Quantitative determination is obtained by contacting the coated solid support with a labeled material, preferably one that reacts specifically with human immunoglobulin. The labeled material used in the immunoassay may be any conventional enzyme covalently linked to an immunological component known to the art. Enzymes suitable for use with the present invention include catalase, peroxidase, urease, glucose oxidase and alkaline phosphatase.

The substrate selected to react with the enzyme can be acted upon by an enzyme to produce a reaction product. Where alkaline phosphatase is the enzyme, a preferred substrate is PNPP (P-nitrophenyl phosphate). The reaction product generated by the action of alkaline phosphatase on PNPP is p-nitrophenol, a yellow substrate that can be measured spectrophotometrically at 405 nM. (S. L. Snyder, et al., *Biochem. Biophys. Acta* 258:178–187, 1972). Other substrates suitable for use with alkaline phosphatase include 4-methyl umbelliferyl phosphate, alpha-naphthyl phosphate, flavone-3-diphosphate and thymolphthalein.

The amount of substrate reaction product and the intensity of color produced will be direct functions of the amount of enzyme conjugate bound to the support plate. Therefore, a measure of substrate reaction product is a measure of the heparin-induced antibody which has been bound to the solid support. The measure is determined by obtaining an optical density (OD) of the reaction product formed on the solid support. The OD of an unknown plasma or serum is contrasted with a control OD determination of a known normal plasma or serum as part of the described assay. If the OD readings are substantially the same, the suspect plasma/serum will not contain antibody to the complex. However, if the suspect plasma/serum OD reading is at least 3 SD greater than the average obtained with normal serum, the plasma/serum donor has HITP or is at risk of developing it.

Preferable controls include using PF4 alone to check for reactivity against PF4 alone seen occasionally in normal subjects and use of excess heparin to inhibit a specific positive reaction.

Other methods are suitable for the detection of HITP antibodies bound to synthetic polymer/PF4 complexes. In one method, red blood cells (or other particles) are coated with polyclonal or monoclonal antibodies specific for human IgG, IgM, or IgA (Y. Shibata, et al., *Vox Sang* 41:25–31, 1981). Adhesion of these red cells to complexes consisting of HITP antibody bound to immobilized synthetic polymer/PF4 complexes is then utilized to indicate the presence of bound HITP antibody.

Alternatively, latex particles or other particulate material can be coated with synthetic polymer/PF4 complexes using the method of the present invention, and HITP antibodies can be detected by their ability to promote agglutination of these coated particles, either directly or after addition of a secondary anti-immunoglobulin reagent. Beads coated with synthetic polymer/PF4 may be used to detect HITP antibodies in a flow cytometric assay.

F. Diagnostic Kit

Diagnostic applications may be implemented according to the present invention in the form of a kit containing complexes which undergo a reaction with a sample of a patient's blood. The kit preferably includes a solid support, such as a microtiter tray, containing wells coated with the synthetic polymer/PF4 complex by the method described above.

The desiccated complexes can be stored for a long period of time, at least 6 months. The kit preferably includes a receptacle containing a chemical label, such as alkaline phosphatase-labeled, goat anti-human IgG (H+L), mouse anti-human IgG, IgA, and IgM and a receptacle containing a suitable substrate, such as p-nitrophenyl phosphate.

A receptacle containing Ecteola cellulose for removing residual heparin may also be included.

EXAMPLES

In General

The present invention is further described by reference to the following, illustrative examples. The contents of the publication by Visentin, et al., *J. Clin. Invest.* 93:81–88, 1994, are hereby incorporated by reference. (Visentin, et al. does not embody the present invention and is cited herein to provide examples of platelet and PF4 isolation techniques.) The Examples utilize plasma samples from 12 patients who developed thrombocytopenia with or without thrombosis while receiving heparin therapy and whose plasma had tested positive in the serotonin release test for heparin-induced antibodies.

Examples 1 and 2 describe the isolation of platelets and the purification of platelet factor 4. Examples 3 and 4 demonstrate the efficacy of a polyvinyl sulfate/PF4 complex in the detection of HITP. Examples 5–12 disclose results with other compounds.

Example 1

Isolation of Platelets

Platelets were isolated from freshly collected blood anti-coagulated with acid citrate dextrose sufficient to produce a pH of 6.4–7.2, with an optimum pH of 6.5, and were washed once in RCD buffer (Ringer's citrate dextrose containing 0.108 mol/liter NaCl 0.038 mol/liter KCl, 0.0017 mol/liter $NaHCO_3$, 0.0212 mol/liter $Na_3C_6H_5O_7.2H_2O$, 0.0278 mol/liter $C_6H_{12}O_6$, 0.011 mol/liter $MgCl_2O.6H_2O$) at pH 6.5 (6.4–7.2) containing 50 μg/ml $PGE_1$ (from Sigma Chemical Company, St. Louis, Mo.).

Example 2

Purification of PF4

PF4 was purified according to Medici, et al., *Thrombo. Res.* 54:277–287, 1989, the contents of which are hereby incorporated by reference, with minor modifications. 10 U of platelets (aged less than or equal to 1 day old) from randomly chosen whole blood donors was pooled. The platelet-rich plasma was pelleted at 1200 g, washed once in RCD buffer at a pH of 6.5 (6.4–7.3) containing EDTA, 0.002 M, and resuspended in PBS (buffer containing 0.02 M/liter, pH 7.2 with 0.145 M/liter NaCl) containing 0.001 M $CaCl_2$, and 0.0014 M PMSF (from Sigma Chemical Company, St. Louis, Mo.) in dimethyl sulfoxide at a concentration of $10^{10}$ platelets/ml in a total volume of 50 ml.

PF4 release was induced with TRAP 11 (thrombin receptor activating peptide) (Peptide Core Lab, Blood Research Institute, Milwaukee, Wis.) at a final concentration of 5 μM for 10–20 minutes at 37° C. with occasional shaking. The activated platelets were then pelleted at 3000 g for 30 minutes at 4° C. (2–8° C.). Ammonium sulfate was slowly added to the supernatant at 60% saturation and the mixture was incubated at 4° C. (2–8° C.) overnight (4–16 hours). The precipitate was discarded and the final supernatant was dialyzed against PBS at 4° C. The dialyzed supernatant (approximately 250 ml) was then incubated with 10 ml of packed heparin-Agarose beads for 4 hours at 4° C. (2–8° C.) with gentle stirring. The beads were washed sequentially with three volumes each of 0.145 M PB-NaCl, 0.8 M PB-NaCl (to remove beta-thromboglobulin and thrombospondin) and resuspended in 10 ml of 1.6 M PB-NaCl to release bound PF4. The final eluate was concentrated using Centriprep 10 (Amicon, Beverly, Mass.) to a 5-ml volume, dialyzed against PBS at 4° C. and treated for 1 hour at 4° C. (2–8° C.) with an excess (70 mg) of ecteola cellulose (from Sigma Chemical Corp., St. Louis, Mo.) equilibrated in PBS to remove residual anti-thrombin-III. The supernatant was then centrifuged and was electrophorised in a 15% SDS—polyacrylamide gel and stained with coomassie blue. A single band corresponding to the PF4 monomer of approximately 7.8 kD was identified. The purified PF4 was stored at 4° C. in 0.0014 M PMSF and 0.05% sodium azide (from Sigma Chemical Company, St. Louis, Mo.).

Example 3

In order to establish the optimum ratio of polyvinyl sulfate to PF4 suitable for the detection of heparin-induced antibodies, various concentrations of polyvinyl sulfate ranging from 0.15 to 1500 microgram per ml were mixed with 10 μg/ml of PF4 in PBS. Fifty microliters of concentrations of polyvinyl sulfate/PF4 complexes were added to wells of a polystyrene microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS.

Fifty microliter aliquots of the diluted samples were added in duplicate to microtiter wells coated with various concentrations of polyvinyl sulfate/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 2:
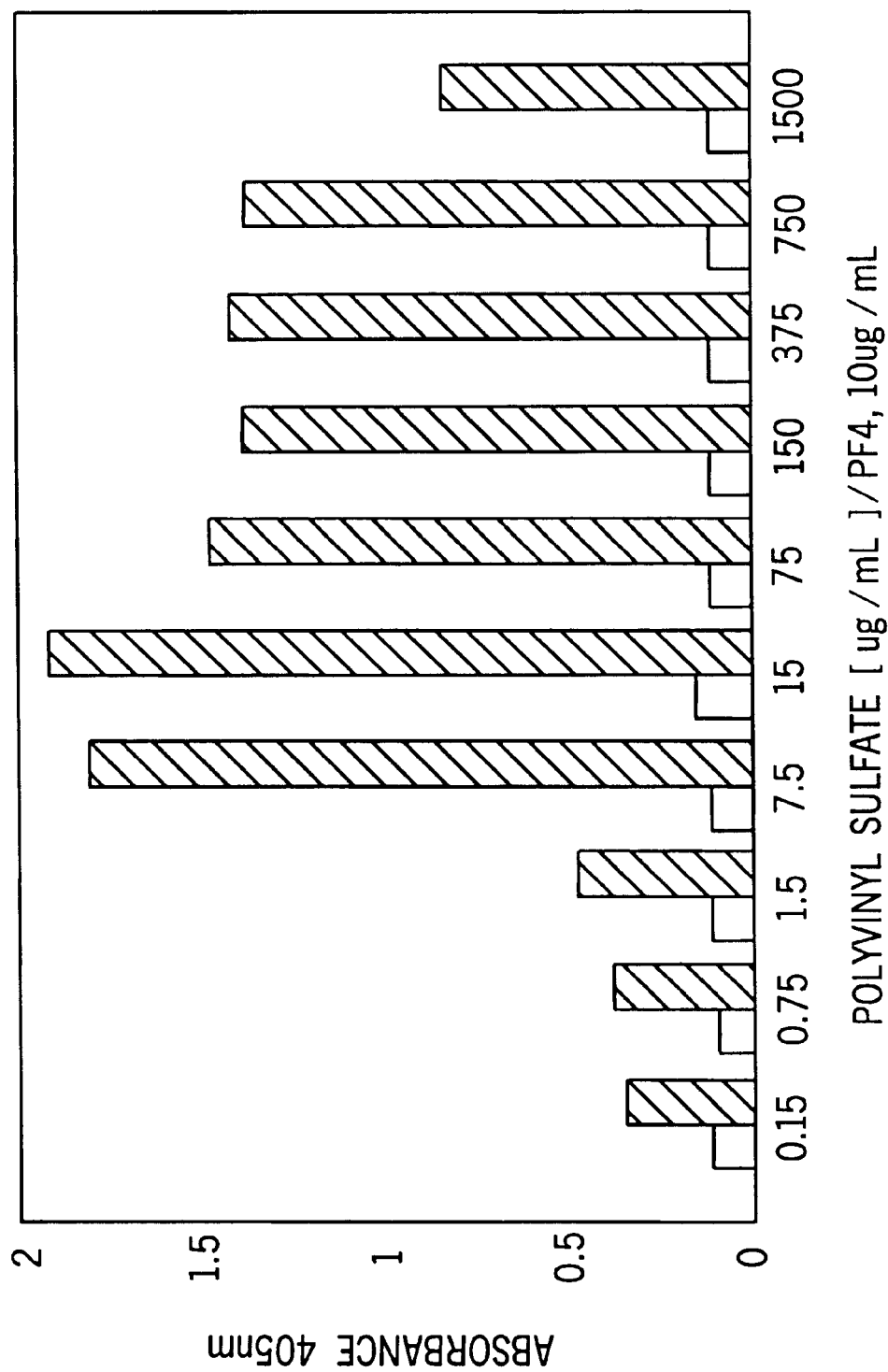
FIG. 2 is a bar graph comparing optical density measurements taken after a patient sample (dark bar) and a normal serum sample (open bar) were added to immobilized polyvinyl sulfate/PF4 complexes prepared by mixing PF4 (10 µg/ml) with different amounts of polyvinyl sulfate.

The results are diagrammed in FIG. 2, which indicates that polyvinyl sulfate can be complexed to PF4 at a wide range of concentrations which are capable of binding to heparin-induced antibodies. Optimally, 7.5 μg/ml–750.0 μg/ml of polyvinyl sulfate should be mixed with 10 μg/ml PF4. Referring to FIG. 2, the shaded bars represent reactions of positive samples. Clear bars represent the reactions of normal samples.

Example 4a

Polyvinyl sulfate (Sigma Chemical Company, St. Louis, Mo., USA) and PF4 were mixed in PBS at a ratio of 7.5 μg/ml polyvinyl sulfate to 10 μg/ml PF4. Fifty microliter aliquots of polyvinyl sulfate/PF4 complex were added of polystyrene microtiter plates (Polysorp; NUNC, DENMARK) and incubated overnight (4–16 hours) at 4° C. (4–8° C.). The microtiter plates were washed three times with PBS-Tw (PBS with 0.05% Tween-20) and blocked for 1 hour at room temperature (20–25° C.) with PBS-Tw-1% BSA (bovine serum albumin). Plasma samples from 12 patients known to contain heparin-induced antibodies were tested in parallel with plasma sample obtained from a normal donor.

Fifty microliters of plasma diluted 1:100 in PBS were added to wells of the microtiter plate (each sample tested in duplicate). In addition, one plasma sample known to contain a strong heparin-induced antibody was diluted 1:500 in PBS and used as positive control. The microtiter plate was incubated at room temperature (20–25° C.) for 1 hour. After 3 washes with PBS-Tw, bound IgG, IgM or IgA was detected by adding alkaline phosphatase-labelled goat anti-human IgG/IgA/IgM diluted 1:2000 in PBS, followed by incubation for 1 hour ar room temperature. After 4 washes with PBS-Tw, the microtiter plate was incubated with P-nitrophenyl phosphate (PNPP) substrate for about 30 minutes at room temperature. The reaction was stopped by addition of 3 M NaOH and absorbance was read at 405 nm using 650 nm for reference values. Reactions were considered positive when the mean optical density (OD) obtained for a sample was at least 3 SD greater than the average obtained with normal control serum.

Figure 3:
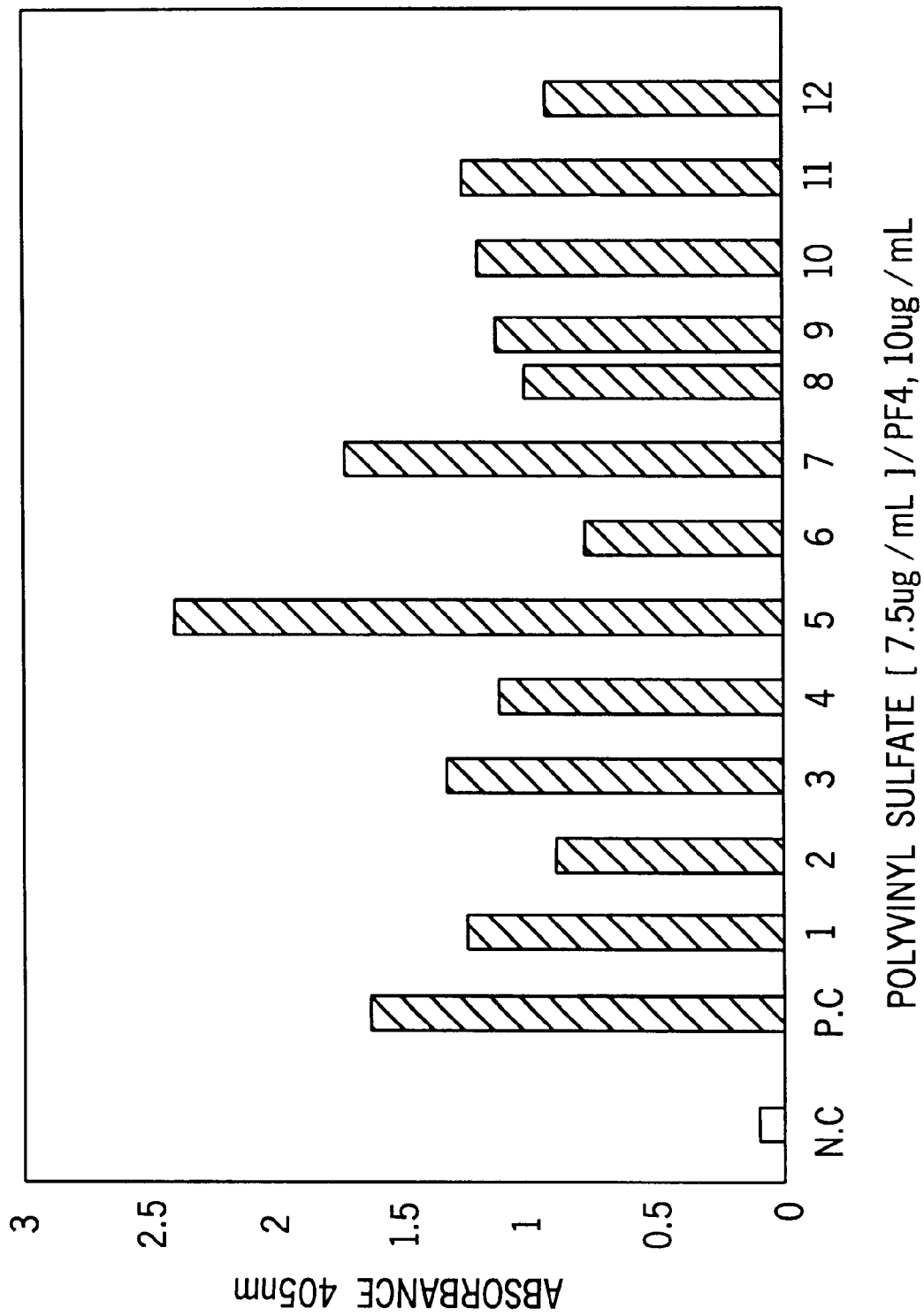
FIG. 3 is a bar graph comparing optical density obtained from 12 different patient samples, a normal control (NC) and a positive control (PC) exposed to an immobilized polyvinyl sulfate/PF4 complex.

FIG. 3 illustrates the results. All twelve HITP patients and the positive control tested positive. The negative control tested negative.

Example 4b

Polyvinyl Sulfonic Acid

Polyvinyl sulfonic acid, sodium salt, formula $(C_2H_4O_3S)_{n\cdot n}Na$, wherein n~ 20 (Polysciences Inc., Warrington, Pa., USA) was evaluated for the present invention. This product, like polyvinyl sulfate (PVS), also binds to platelet factor 4 (PF4) to form a complex at a wide range of concentrations, and has the added advantage of having a lower background signal. PVS/PF4 complexes are more stable than heparin (HEP)/PF4 complexes at higher temperatures, e.g. when ELISA test procedures are carried out at 37° C., PVS/PF4 complexes produce higher optical density readings than HEP/PF4 complexes tested under the same conditions. This is presumably because HEP/PF4 complexes are unstable at 37° C. or higher temperatures.

Example 5

In order to establish the optimum ratio of polyvinyl sulfonate (PVS) to PF4 suitable for the detection of heparin-induced antibodies, various concentrations of polyvinyl sulfonate (molecular weight 2000–6000) ranging from 1.0 to 800 microgram per ml were mixed with 10 μg/ml of PF4 in PBS. Fifty microliter aliquots of the mixtures containing polyvinyl sulfonic/PF4 complexes were added to wells of a microtiter plate (POLYSORP; NUNC, DENMARK) and incubated overnight at 4° C. (2–8° C). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of polyvinyl sulfonate/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 4:
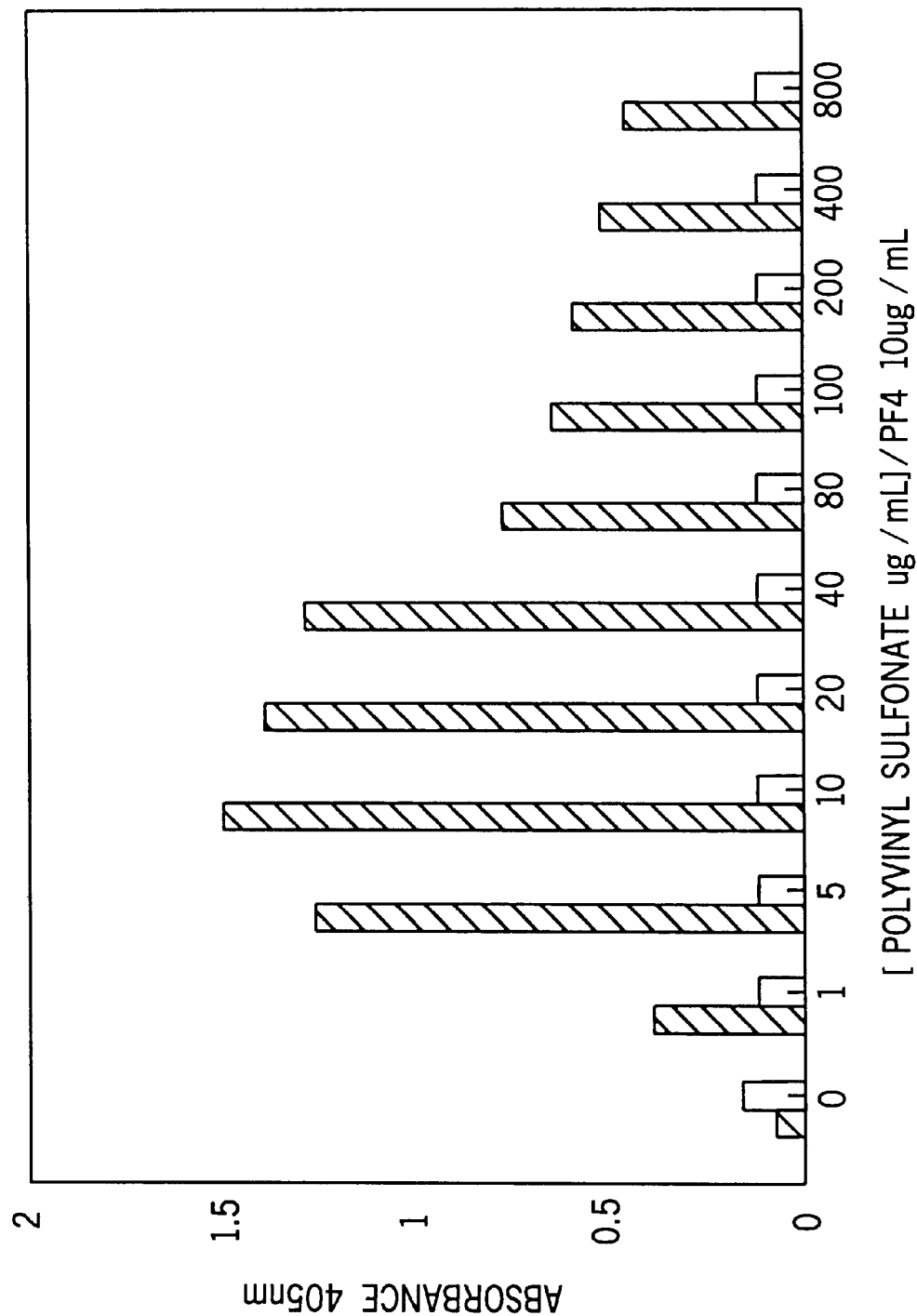
FIG. 4 is a bar graph comparing optical density obtained from positive (dark bar) and negative (open bar) patient samples exposed to immobilized polyvinyl sulfonate/PF4 complexes prepared by mixing PF4 (10 µg/ml) with different amounts of polyvinyl sulfonate.

The results are diagrammed in FIG. 4, which indicates that polyvinyl sulfonate of molecular weight of 2000–6000 can be complexed to PF4 at a range of concentrations which are capable of binding to heparin-induced antibodies. Optimally, 2.0 μg/ml–10.0 μg/ml of polyvinyl sulfonic acid should be mixed with 10 μg/ml PF4.

Referring to FIG. 4, the shaded bars represent reactions of positive samples. Clear bars represent reactions of normal samples.

Example 6

Polyvinyl sulfonic acid, sodium salt, formula $(C_2H_4O_3S)_n \cdot_n Na$ where n~ 20 (Polysciences, Inc., Warrington, Pa., USA) and PF4 were mixed in PBS at a ratio of 5 μg/ml polyvinyl sulfonic acid to 10 μg/ml PF4. Fifty microliter aliquots of polyvinyl sulfonic acid/PF4 complex were added of polystyrene microtiter plates (Polysorp; NUNC, DENMARK) and incubated overnight (4–16 hours) at 40° C. (4–8° C.). The microtiter plates were washed three times with PBS-Tw (PBS with 0.05% Tween-20) and blocked for 1 hour at room temperature (20–25° C.) with PBS-Tw-1% BSA (bovine serum albumin). Plasma samples from 9 patients known to contain heparin-induced antibodies were tested in parallel with plasma sample obtained from a normal donor.

Fifty microliters of plasma diluted 1:50 in PBS were added to wells of the microtiter plate (each sample tested in duplicate). In addition, one plasma sample known to contain a strong heparin-induced antibody was diluted 1:500 in PBS and used as positive control. The microtiter plate was incubated at 37° C. for 30 minutes. After 4 washes with PBS-Tw, bound IgG, IgM or IgA was detected by adding alkaline phosphatase-labelled goat anti-human IgG/IgA/IgM diluted 1:2000 in PBS, followed by incubation for 30 minutes at 37° C. After 4 washes with PBS-Tw, the microtiter plate was incubated with P-nitrophenyl phosphate (PNPP) substrate for about 30 minutes at room temperature. The reaction was stopped by addition of 3 M NaOH and absorbance was read at 405 nm using 650 nm for reference values. Reactions were considered positive when the mean optical density (OD) obtained for a sample was at least 3 SD greater than the average obtained with normal control serum.

Figure 5:
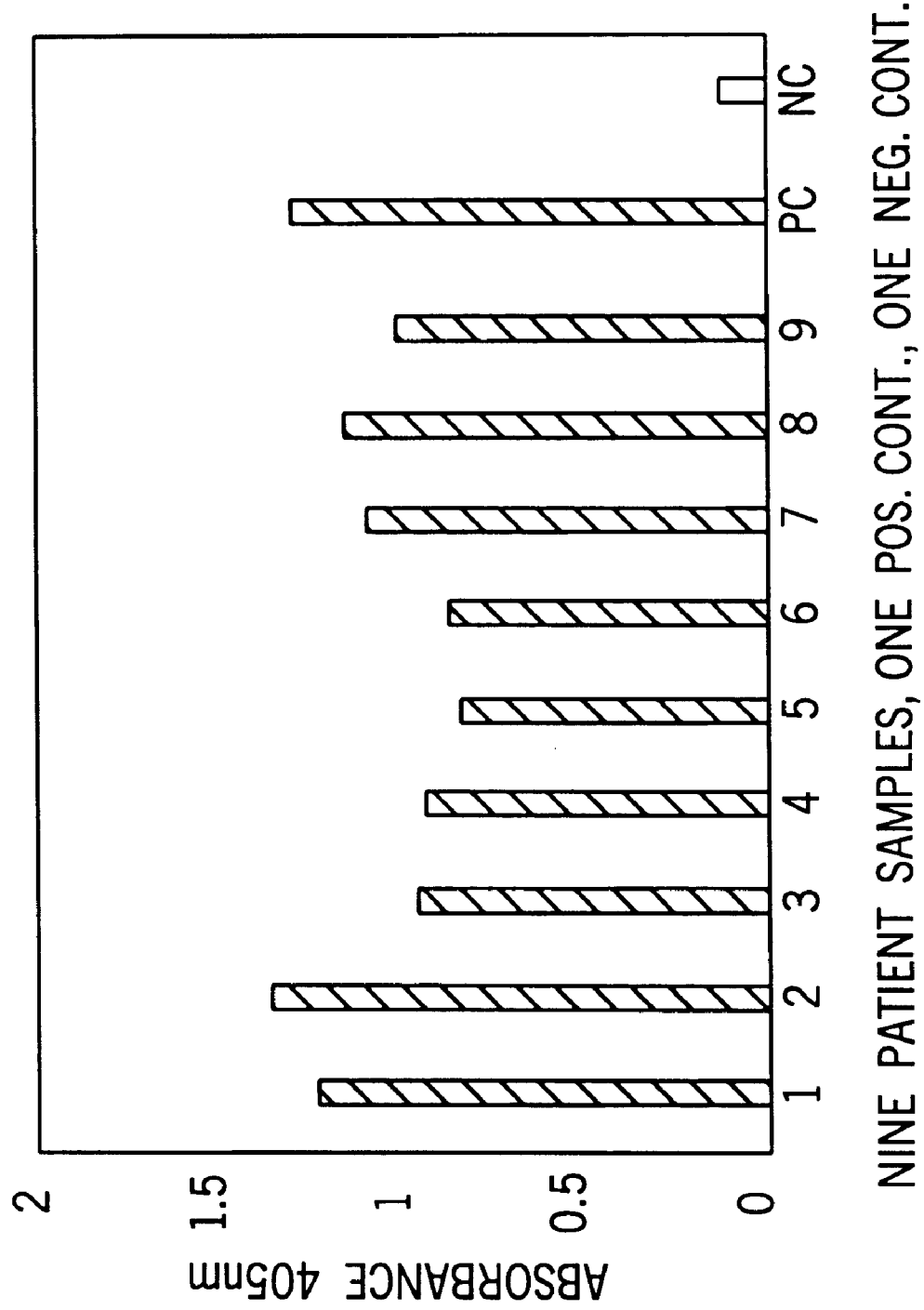
FIG. 5 is a bar graph comparing optical density obtained from 9 different patient samples (dark bars), a positive control (shaded bar) and a normal control (open bar) sample exposed to an immobilized polyvinyl sulfonate/PF4 complexes.

FIG. 5 illustrates the results. All nine HITP patients and the positive control tested positive. The negative control tested negative. Referring to FIG. 5, the shaded bars represent reactions of positive samples. Clear bars represent reactions of normal samples.

Example 7

Polystyrene Sulfonate

Poly(sodium 4-styrene sulfonate) [—CH$_2$CH(C$_6$H$_4$SO$_3$Na)—]$_N$, average molecular weight 70,000, was obtained from Aldrich, Milwaukee, Wis. USA.

In order to establish the optimum ratio of poly(sodium 4-styrene sulfonate) to PF4 suitable for the detection of heparin-induced antibodies, various concentrations of polystyrene sulfonate ranging from 0.07 to 700 microgram per ml were mixed with 10 μg/ml of PF4 in PBS and allowed to stand at room temperature for 30 minutes. Fifty microliters of concentrations of polystyrene sulfonate/PF4 complexes were added to wells of a microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of polystyrene sulfonate/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 6:
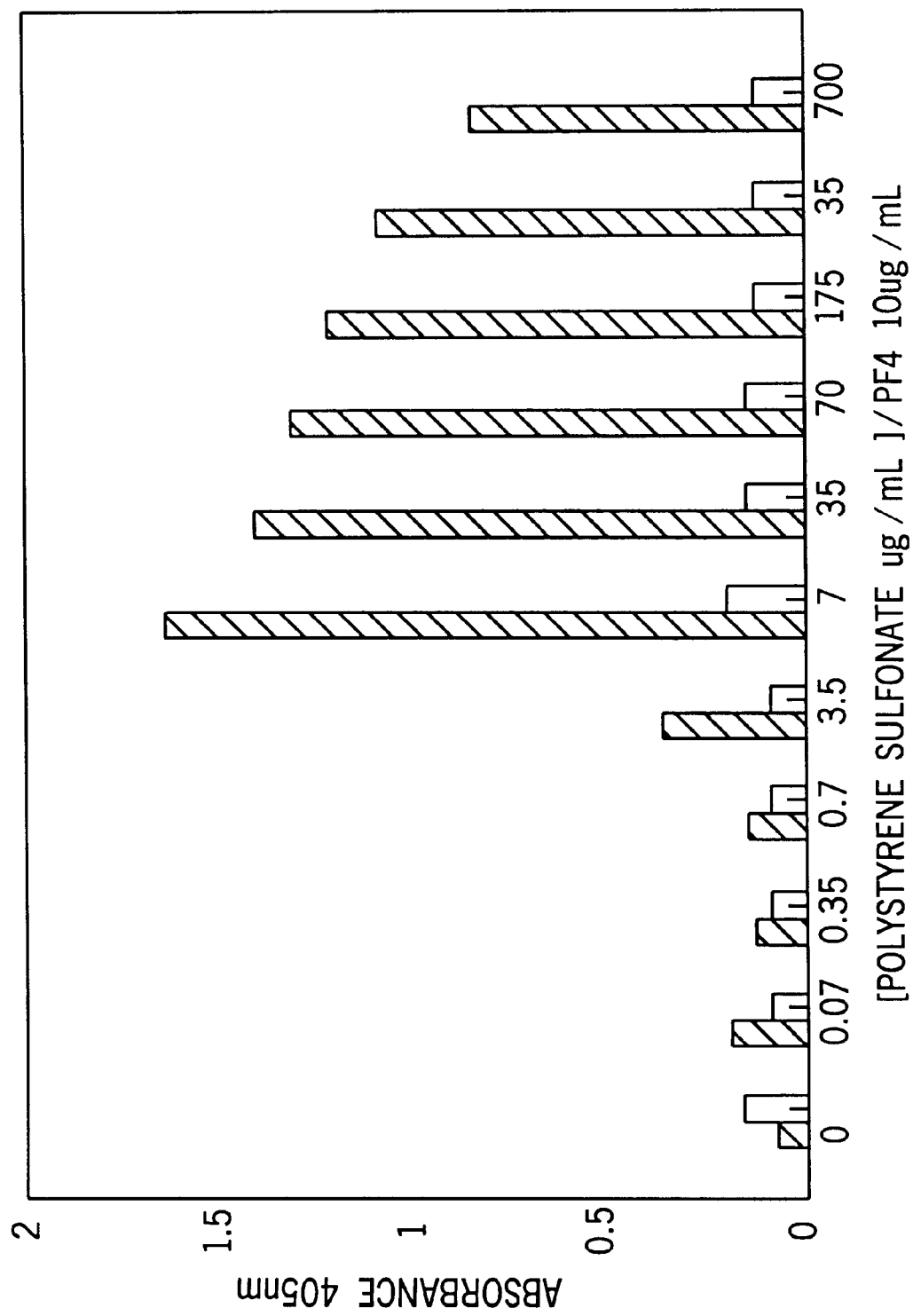
FIG. 6 is a bar graph comparing optical density obtained after a patient sample (dark bars) and a normal serum sample (open bars) were added to immobilized polystyrene sulfonate/PF4 complexes prepared by mixing PF4 (10 µg/ml) with different amounts of polystyrene sulfonate.

The results are diagrammed in FIG. 6, which indicate that polystyrene sulfonate can also be complexed to PF4 at a wide range of concentrations which are capable of binding to heparin-induced antibodies. Optimally, 7.0 μg/ml–700.0 μg/ml of polystyrene sulfonate should be mixed with 10 μg/ml PF4. Referring to FIG. 6, the shaded bars represent reactions of positive samples. Clear bars represent reactions of normal samples.

Example 8

Polyanetholesulfonic Acid

Polyanetholesulfonic acid sodium salt (sodium polyanetholesulfonate) was obtained from Sigma Chemical Company, St. Louis, Mo.

In order to establish the optimum ratio of sodium (polyanetholesulfonic acid) to PF4 suitable for the detection of heparin-induced antibodies, various concentrations of polyanetholesulfonic acid ranging from 0.15 to 1500 microgram per ml were mixed with 10 μg/ml of PF4 in PBS. Fifty microliters of concentrations of sodium polyanethole sulfonate/PF4 complexes were added to wells of a microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of sodium polyanethole sulfonate/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 7:
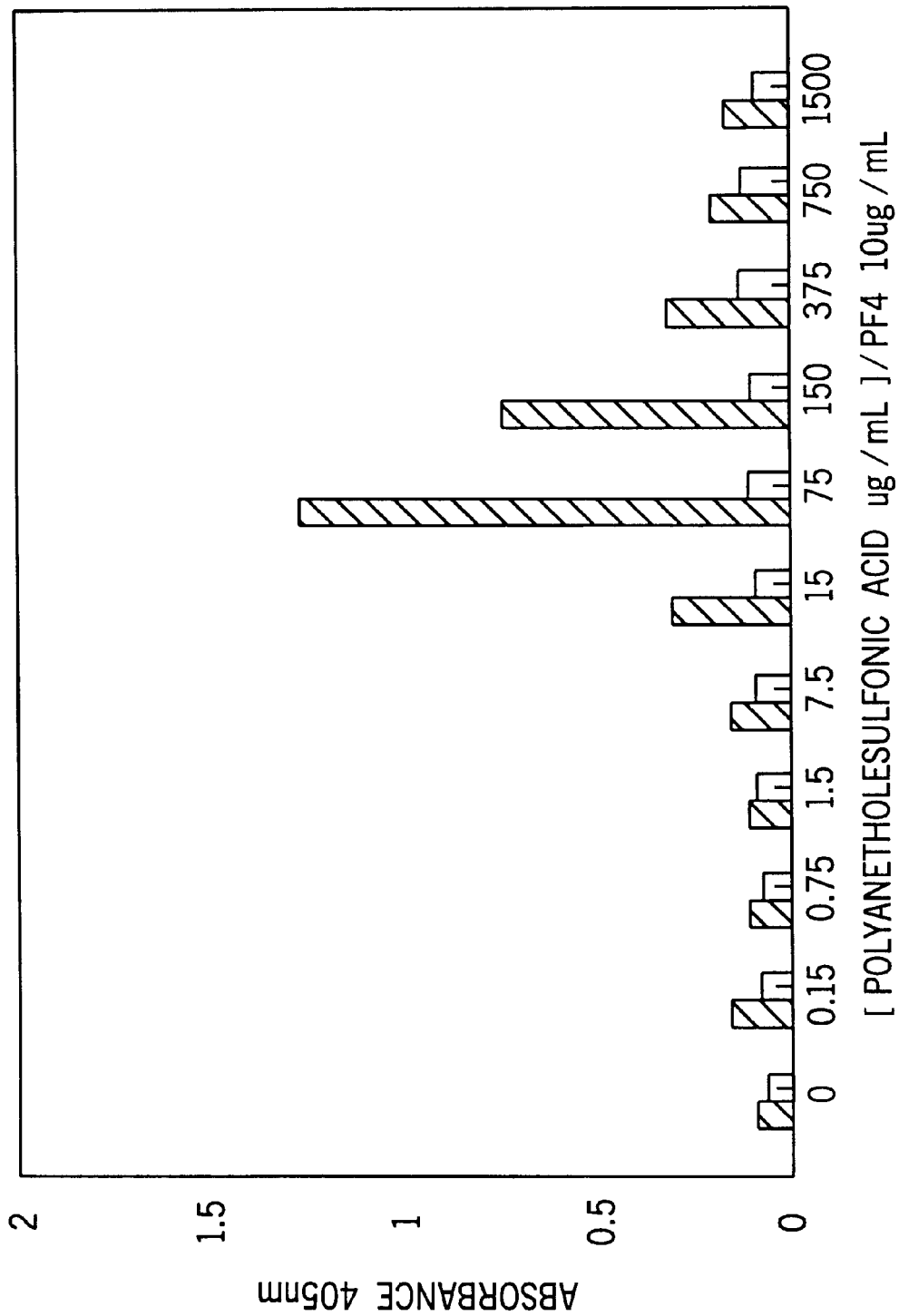
FIG. 7 is a bar graph comparing optical density obtained after a patient sample (dark bars) and a normal sample (open bars) were added to immobilized polyanetholesulfonic acid/PF4 complexes prepared by mixing PF4 (10 µg/ml) with different amounts of polyanetholsulfonate.

The results are diagrammed in FIG. 7, which indicates that polyanethole sulfonic acid can be complexed to PF4 at a range of concentrations between 75–150 $\mu$g/ml which are capable of binding to heparin-induced antibodies. Optimally, 50 $\mu$g/ml–150 $\mu$g/ml of polyanethole sulfonic acid should be mixed with 10 $\mu$g/ml PF4. Referring to FIG. 7, shaded bars represent reactions of positive samples. Clear bars represent reactions of normal samples.

Example 9

Polyvinyl Phosphate

Polyvinyl phosphoric acid sodium salt was obtained from Polysciences Inc., Warrington, Pa., USA. In order to establish the optimum ratio of polyvinyl phosphate to PF4 suitable for the detection of heparin-induced antibodies, various concentrations of polyvinyl phosphate ranging from 1–800 microgram per ml were mixed with 10 $\mu$g/ml of PF4 in PBS. Fifty microliters of concentrations of polyvinyl phosphate/PF4 complexes were added to wells of a microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of polyvinyl phosphate/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 8:
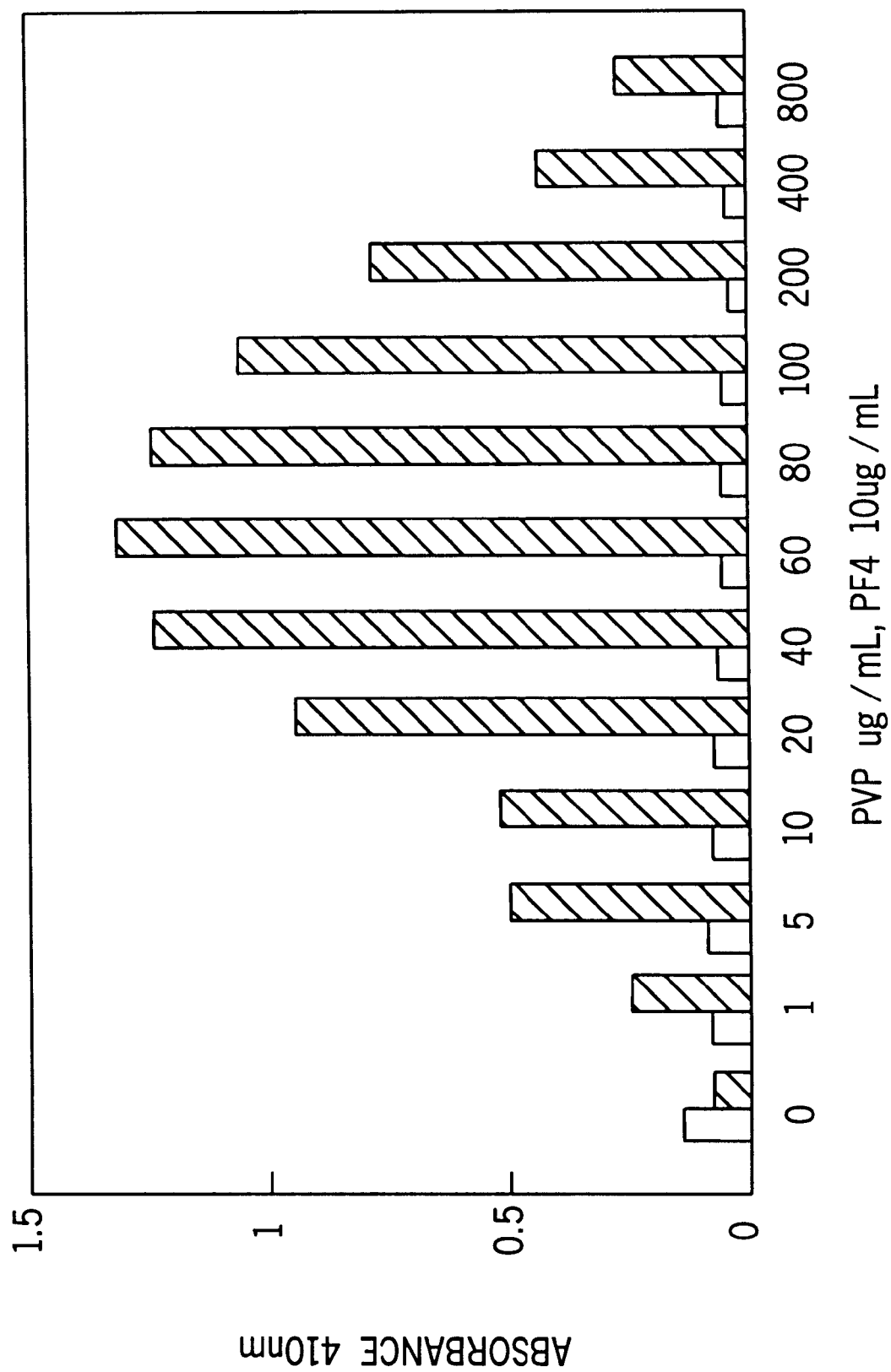
FIG. 8 is a bar graph comparing optical density obtained after a patient sample (dark bars) and a normal sample (open bars) were added to immobilized poly(vinylphosphoric acid)/PF4 complex prepared by mixing PF4 (10 µg/ml) with different amounts of poly(vinylphosphoric acid) (PVP).

The results are diagrammed in FIG. 8, which indicates that polyvinyl phosphate can be incubated with PF4 at a wide range of concentrations to produce complexes that are capable of binding to heparin-induced antibodies. Optimally, 4 $\mu$g/ml–400 $\mu$g/ml of polyvinyl phosphate should be mixed with 10 $\mu$g/ml PF4. Referring to FIG. 8, shaded bars represent reactions of positive samples. Clear bars represent reactions of normal samples.

Example 10

Polyvinylphosphonic Acid

Poly(vinylphosphonic acid) was obtained from Polysciences Inc., Warrington, Pa., USA.

In order to establish the optimum ratio of poly (vinylphosphonic acid) to PF4 suitable for the detection of heparin-induced antibodies, various concentrations of poly (vinyl phosphonic acid) ranging from 1 to 800 microgram per ml were mixed with 10 $\mu$g/ml of PF4 in PBS. Fifty microliters of concentrations of polyvinyl sulfate/PF4 complexes were added to wells of a microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of poly(vinylphosphonic acid)/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 9:
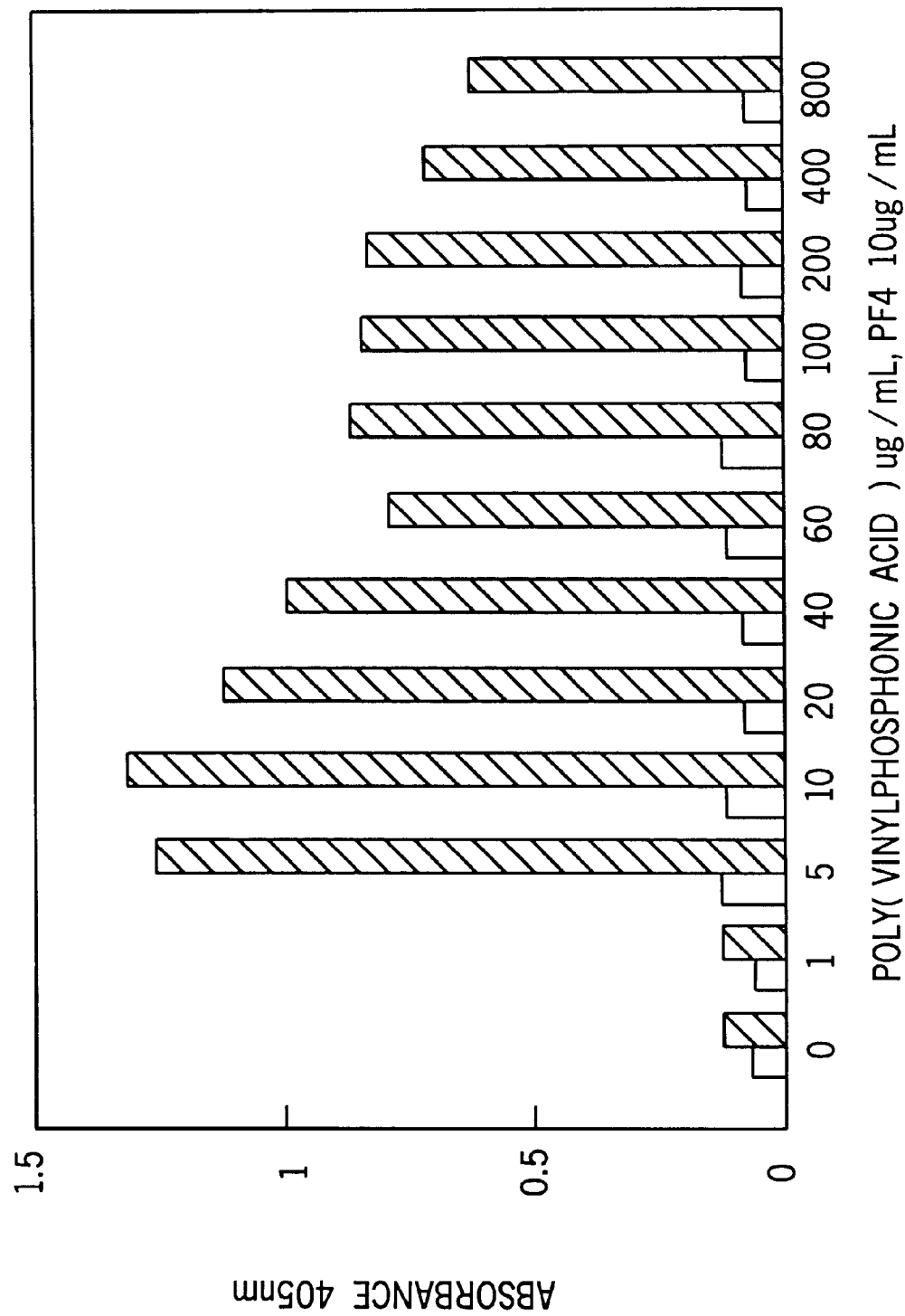
FIG. 9 is a bar graph comparing optical density obtained from both positive (dark bars) and negative (open bars) patient samples exposed to different amounts of immobilized poly(vinyl phosphonic acid)/PF4 (10 µg/ml) complexes.

The results are diagrammed in FIG. 9, which indicates that polyvinylphosphonic acid can be complexed to PF4 at a wide range of concentrations which are capable of binding to heparin-induced antibodies. Optimally, 5 $\mu$g/ml–400 $\mu$g/ml of polyvinylphosphonic acid should be mixed with 10 $\mu$g/ml PF4. Referring to FIG. 9, the shaded bars represent reactions of positive samples. Clear bars represent reactions of normal samples.

Example 11

Poly-D-Glutamic Acid

Poly-D-glutamic acid, sodium salt was obtained from Sigma Chemical Company, St. Louis, Mo., molecular weight approximately 2000–15000 [—NHCH (CH$_2$CH$_2$CO$_2$Na)CO—]$_n$.

In order to establish the ratio of poly-D-glutamic acid to PF4 suitable for the detection of heparin-induced antibodies, various concentrations of poly-D-glutamic acid ranging from 0.01 to 100 microgram per ml were mixed with 10 $\mu$g/ml of PF4 in PBS. Fifty microliters of concentrations of poly-D-glutamic acid/PF4 complexes were added to wells of a microtiter plate (POLYSORP; NUNC, DENMARK) and incubated overnight at 4° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of poly-D-glutamic acid/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

Figure 10:
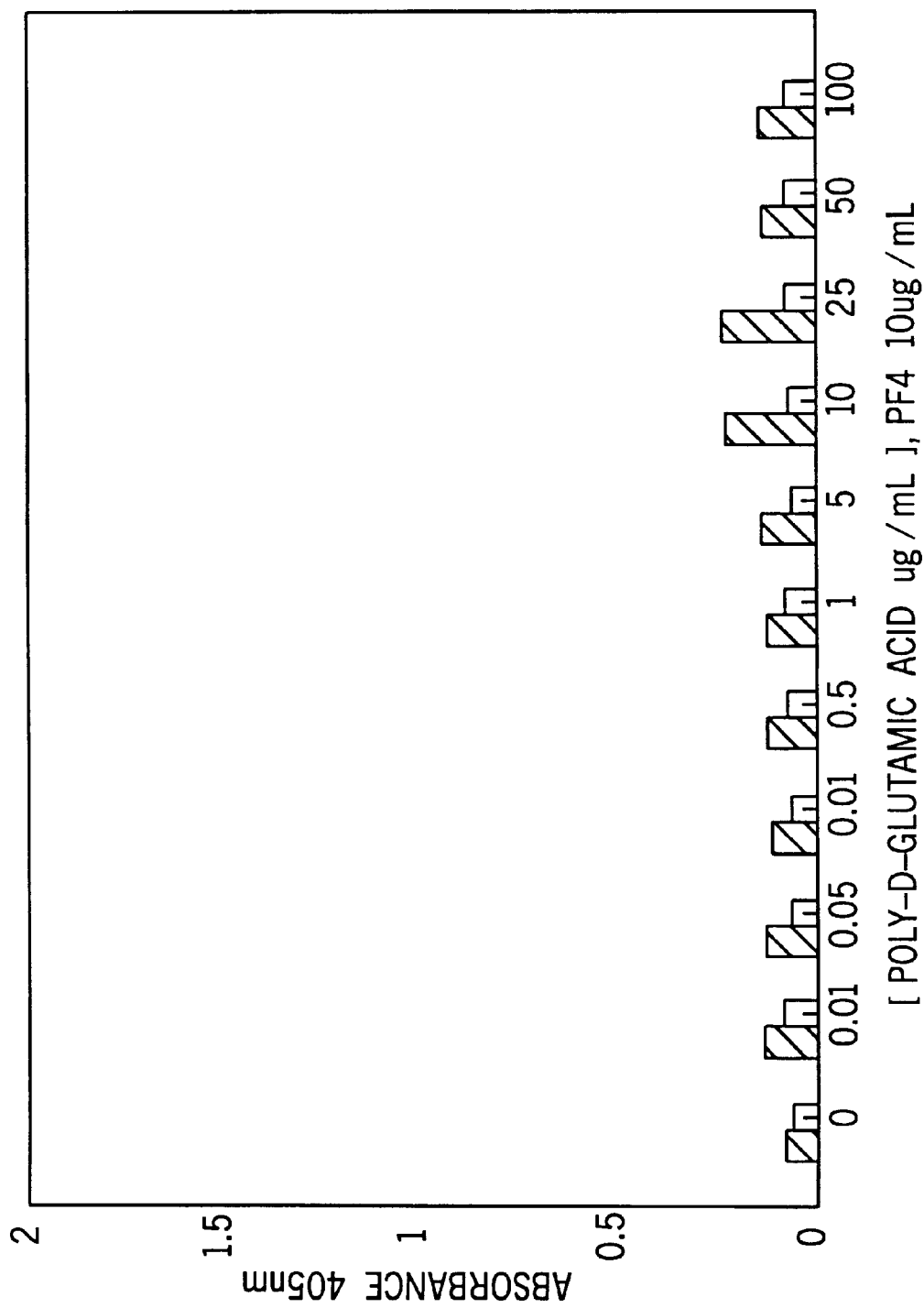
FIG. 10 is a bar graph comparing optical density obtained after a patient sample (dark bars) and a normal sample (open bars) were added to immobilized poly-D-glutamic acid/PF4 complex prepared by mixing PF4 (10 µg/ml) with different amounts of poly-D-glutamic acid.

The results are diagrammed in FIG. 10 which indicates that poly-D-glutamic acid cannot be successfully complexed to PF4 at even a narrow range of concentrations which are capable of binding to heparin-induced antibodies. Referring to FIG. 10, shaded bars represent reactions of positive samples. Clear bars represent reactions of normal samples.

Example 12

Polyethylene Glycol

Polyethylene glycol was obtained from Fluka (New York) with molecular weight approximately 4000 (3000–4500) $H(OCH_2CH_2)nOH$.

In order to establish the optimum ratio of polyethylene glycol to PF4 suitable for the detection of heparin-induced antibodies, various concentrations of polyethylene glycol ranging from 0.004 to 40 microgram per ml were mixed with 10 µg/ml of PF4 in PBS. Fifty microliters of concentrations of polyethylene glycol/PF4 complexes were added to wells of a microtiter plate (POLYSORP; NUNC, DENMARK) and incubated overnight at 40° C. (2–8° C.). The microtiter plate was then washed three times with PBS-Tw (PBS with 0.05% Tween-20) and blocked for 1 hour at room temperature (20–25° C.) with PBS-Tw-1% BSA (bovine serum albumin).

One patient sample known to have a strong heparin-induced antibody was diluted 1:500 in PBS, and one plasma sample from a normal donor was diluted 1:100 in PBS. Fifty microliter aliquots of the diluted samples were added in duplicate to microtiter wells coated with various concentrations of polyethylene glycol/PF4 complexes and incubated for 1 hour at room temperature (20–25° C.). After three washes with PBS-Tw, bound IgG was detected by adding alkaline phosphatase labelled anti-human IgG diluted 1:2000 in PBS, followed by incubation for 1 hour at room temperature. After four washes with PBS-Tw, the microtiter plate was incubated with P-nitrophenyl phosphate (PNPP) substrate for about 30 minutes at room temperature. The reaction was stopped by the addition of 3 M NaOH and absorbance was read at 405 nm using 650 nm for reference values.

The results are diagrammed in FIG. 11, which indicates that polyethylene glycol can not successfully be complexed to PF4 to form complexes that are capable of binding to heparin-induced antibodies. Higher concentration of polyethylene glycol tend to precipitate PF4. Referring to FIG. 11, shaded bars represent reactions of positive samples. Clear bars represent reactions of normal samples.

We claim:

1. A method of detecting heparin-induced antibodies to screen for heparin-induced thrombocytopenia, comprising:
    (a) binding human platelet factor 4 to a linear, non-glycosaminoglycan polymer having a backbone and carrying negative charges distributed along the polymer chain wherein the negative charge carried by each subunit of the polymer is less than 10 Å from the polymer chain backbone, wherein the polymer comprises between 10 and 60 subunits, is between 2–6,000 Daltons in molecular mass and wherein the polymer is selected from the group consisting of polyvinyl sulfonate, polystyrene sulfonate, polyanetholesulfonate, polyvinyl phosphate, polyvinyl phosphonate and polyvinyl sulfate, whereby complexes having an epitope recognizable by antibodies generated in heparin-induced thrombocytopenia are formed;
    (b) contacting blood plasma or serum from a human patient suspected of having heparin-induced thrombocytopenia with the complexes; and (c) analyzing the complexes to detect the heparin-induced antibodies.

2. The method of claim 1 wherein the polymer is selected from the group consisting of polyvinyl sulfate and polyvinyl sulfonate.

3. The method of claim 1 wherein the platelet factor 4 is selected from the group consisting of native platelet factor 4 and recombinant platelet factor 4.

4. The method of claim 1 wherein the platelet factor 4 is synthetic platelet factor 4.

5. The method of claim 1 wherein step b or step c is at 37° C.

6. A kit for diagnosing HITP comprising the polymer/PF4 complexes attached to a solid support, wherein the complexes comprise a polymer selected from the group consisting of polyvinyl sulfonate, polystyrene sulfonate, polyanetholesulfonate, polyvinyl phosphate, polyvinyl phosphonate and polyvinyl sulfate, the polymer having a backbone and carrying negative charges distributed along the polymer chain wherein the negative charge carried by each subunit of the polymer is less than 10 Å from the polymer chain backbone and wherein the polymer comprises between 10 and 60 subunits and is between 2–6,000 Daltons in molecular mass whereby complexes having an epitope recognizable by antibodies generated in heparin-induced thrombocytopenia are formed.

7. The kit of claim 6 additionally comprising a receptacle containing a chemical label for detecting an antibody generated in heparin-induced thrombocytopenia that has bound to the polymer/PF4 complex, wherein the label is selected from the group consisting of an anti-human IgG/enzyme complex, an anti-human IgM/enzyme complex, an anti-human IgA/enzyme complex and a polyvalent probe that recognizes all three immunoglobulins (IgG, IgM, IgA).

* * * * *

UNITED STATES PATENT AND TRADEMARK OFFICE
CERTIFICATE OF CORRECTION

PATENT NO. : 5,972,718
DATED : October 26, 1999
INVENTOR(S) : Manouchehr Moghaddam et al.

It is certified that error appears in the above-identified patent and that said Letters Patent is hereby corrected as shown below:

Column 1,
Line 2, after the title, please insert:

-- Statement Regarding Federally Sponsored Research or Development --
Line 3, please insert:

-- This invention was made with United States government support awarded to the following agency: NIH HL 13629. The United States has certain rights in this invention. --

Signed and Sealed this

Thirtieth Day of September, 2003

JAMES E. ROGAN
*Director of the United States Patent and Trademark Office*